(12) United States Patent
Lin et al.

(10) Patent No.: US 7,544,659 B2
(45) Date of Patent: Jun. 9, 2009

(54) PROMOTION OF AXONAL REGENERATION

(75) Inventors: John (Chia-Yang) Lin, Mountain View, CA (US); Arnon Rosenthal, Woodside, CA (US)

(73) Assignee: Genentech, Inc., South San Francisco, CA (US)

( * ) Notice: Subject to any disclaimer, the term of this patent is extended or adjusted under 35 U.S.C. 154(b) by 212 days.

(21) Appl. No.: 10/917,905

(22) Filed: Aug. 13, 2004

(65) Prior Publication Data
US 2006/0035826 A1    Feb. 16, 2006

(51) Int. Cl.
*A61K 38/17* (2006.01)

(52) U.S. Cl. ............................................ 514/12

(58) Field of Classification Search ............... None
See application file for complete search history.

(56) References Cited

U.S. PATENT DOCUMENTS

| 6,036,957 | A  | * | 3/2000 | Weiner et al. | ............. | 424/184.1 |
| 6,252,040 | B1 | * | 6/2001 | Warren et al. | ............... | 530/328 |
| 2006/0194210 | A1 | * | 8/2006 | Morris | | |

FOREIGN PATENT DOCUMENTS

| WO | 99/14328 | | 3/1999 |
| WO | 99/20644 | * | 4/1999 |
| WO | 99/63088 | | 12/1999 |
| WO | 00/15796 | | 3/2000 |
| WO | 00/73454 | | 12/2000 |
| WO | 01/04311 | | 1/2001 |
| WO | 01/68848 | | 9/2001 |

OTHER PUBLICATIONS

Kandel et al. 1991 Principles of Neural Science, pp. 258-265.*
van Ham 2003. Molecular Biology Reports 30:69-82.*
Bradl 2003. J Neurol Neurosurg Psychiatry 74:1364-1370.*
Deumens 2002. Experimental Neurology 175:303-317.*
Cluskey et al. 2001. Mol Pathol 54:386-392.*
Hoffner et al 2002. Biochimie 84:273-278.*
Lin 2003. Nature Neuroscience 6:1270-1276.*
Gonsette, 2004. Expert Opin Pharmacother. 5(4):747-765.*
Winer, 2002. Q J Med 95:717-721.*
Mittoux 2002. J Neurosci 22:4478-4486.*
Saykin, 2004. Brain 127:1574-1583.*
Schenk 1999. Nature 400:173-177.*
Yuki 2001. Annals of Neurology 49:712-720.*
Leegwater-Kim 2004. NeuroRx 1:128-138.*
Shastry 2003. Neurochemistry International 43:1-4).*
Bates 2003. Curr Opin Neurol 16:465-470.*
Braisted, et al., "Thalamocortical Axons are Influenced by Chemorepellent and Chemoattractant Activities Localized to Decision Points Along Their Path", Developmental Biology, vol. 208, pp. 430-440, (1999).
Hamelin, et al., "Expression of the UNC-5 Guidance Receptor in the Touch Neurons of *C. Elegans* Steers their Axons Dorsally", Nature, vol. 364, pp. 327-330, (1993).
Hedgecock, et al., "The UNC-5, UNC-6, and UNC_40 Genes Guide Circumferential Migrations of Pioneer Axons and Mesodermal Cells on the Epidermis in *C. Elegans*", Neuron, vol. 2, pp. 61-85, (1990).
Ishii, et al., "UNC-6, A Laminin-Related Protein, Guides Cell and Pioneer Axon Migrations in *C. Elegans*", Neuron, vol. 9, pp. 873-881, (1992).
Keino-Masu, et al., "Deleted in Colorectal Cancer (DCC) Encodes a Netrin Receptor", Cell, vol. 87, pp. 175-185, (1996).
Lee, et al., "IL-17E, A Novel Proinflammatory Ligand for the IL-17 Receptor Homolog IL-17Rh1", The Journal of Biological Chemistry, vol. 276, No. 2, pp. 1660-1164, (2001).
Leonardo, et al., "Vertebrate Homologues of *C. Elegans* UNC-5 are Candidate Netrin Receptors", Nature, vol. 386, pp. 833-838, (1997).
Metin, et al., "The Ganglionic Eminence May Be an Intermediate Target for Corticofugal and Thalamocortical Axons", The Journal of Neuroscience, vol. 16, No. 10, pp. 3219-3235, (1996).
Nakashiba, et al., "Netrin-G1: A Novel Glycosyl Phosphatidylinositol-Linked Mammalian Netrin That is Functionally Divergent from Classical Netrins", The Journal of Neuroscience, vol. 20, No. 17, pp. 6540-6550, (2000).
Serafini, et al., "The Netrins Define a Family of Axon Outgrowth-Promoting Proteins Homologous to *C. Elegans* UNC-6", Cell, vol. 78, pp. 409-424, (1994).
Yin, et al., "Laminets: Laminin-and Netrin-Related Genes Expressed in Distinct Neuronal Subsets", Molecular and Cellular Neuroscience, vol. 19, pp. 344-358, (2002).
Bagri, et al., "Slit Proteins Prevent Midline Crossing and Determine the Dorsoventral Position of Major Axonal Pathways in the Mammalian Forebrain", Neuron, vol. 33, pp. 233-248, (2002).
Gold et al., Journal of Neuroimmunology 138: 99-105 (2003).
Villoslada et al. J. Exp. Med. 191:1799-1866 (2000).
Linker et al. Nat. Med. 6: 620-624 (2002).
Bensa et al., Eur. J. Neurol. 7(4):423-6 (2000).
Birecree et al., Journal of Neuropathology and Experimental Neurology: 47(5); pp. 549-560 (1988).
Klein et al., Brain. Res. 875:144-151 (2000).
Holtzman, et al, "Selective Inhibition of Axon Outgrowth by Antibodies to NGF in a Model to Temporal Lobe Epilepsy", The Journal of Neuroscience, 15(11): 7062-7070, (1995).
McDonald, et al, "A model for a glutamate receptor agonist antibody-binding site", Journal of Molecular Recognition, vol. 12, pp. 219-225, (1999).
Steiner, et al, "Neurotrophic immunophilin ligands stimulate structural and functional recovery in neurodegenerative animal models", Proc. Natl. Acad. Aci., vol. 94, pp. 2019-2024, (1997).

\* cited by examiner

*Primary Examiner*—Daniel E. Kolker
(74) *Attorney, Agent, or Firm*—Jennifer L. Elliott; James A. Fox; Ginger R. Dreger

(57) ABSTRACT

The present invention concerns a method of promoting axonal regeneration. In particular, the invention concerns a method of promoting the growth or regeneration of neurons, and treating disease or conditions associated with the loss, loss of function or dysfunction of nerve cells, in particular thalamic nerve cells, by administering a polypeptide having a high degree of sequence identity with a native sequence Netrin G1 (NGL-1) or an agonist thereof.

5 Claims, 12 Drawing Sheets

```
              319       330       340       350       360    371
NGL(317)    KDMAPSNTACCARCNTPPNLKGRYIGELDQNYFTCYAPVIVEPPADLNVTEGM
NAG14(316)  REYIPTNSTCCGRCHAPMHMRGRYLVEVDQASFQCSAPFIMDAPRDLNISEGR
HSM(112)    KETVPSNTTCCARCHAPAGLKGRYIGELDQSHFTCYAPVIVEPPTDLNVTEGM
            ────────────────────────→  ────────────────────────────────────←

372     380       390       400       410      424
NGL(370)    AAELKCRASTSLTSVSWITPNGTVMTHGAYKVRIAVLSDGTLNFTNVTVQDTG
NAG14(369)  MAELKCRTPP-MSSVKWLLPNGTVLSHASRHPRISVLNDGTL FSHVLLSDTG
HSM(165)    AAELKCRTGTSMTSVNWLTPNGTLMTHGSYRVRISVLHDGTLNFTNVTVQDTG
            ───────────────────────────────────────────────
                              Ig DOMAIN 425  430       440       450       460       477
NGL(423)    MYTCMVSNSVGNTTASATLNVTAATTTP--------------------FS
NAG14(421)  VYTCMVTNVAGNSNASAYLNVSTAELNTSN-------------------YS
HSM(218)    QYTCMVTNSAGNTTASATLNVSAVDPVAAGGTGSGGGGPGGSGGVGGGSGGYT
            ──────→

478       490       500       510       520     530
NGL(453)    YFSTVTVETMEPSQ-----DEARTTDNNVGPTPVVDW----------ETTNVT
NAG14(453)  FFTTVTVETTEISP-----EDTTRKYKPVPTTSTGYQ----------PAYTTS
HSM(271)    YFTTVTVETLETQPGEEALQPRGTEKEPPGPTTDGVWGGGRPGDAAGPASSST 531      540       550       560       570     583
NGL(491)    TSLTPQSTRSTEKTFTIPVTDINS-GIPGIDEVMKTTKIIIGCFVAITLMAAV
NAG14(491)  TTVLIQTTRVPKQVAVPATDTTDK-MQTSLDEVMKTTKIIIGCFVAVTLLAAA
HSM(324)    TAPAPRSSRPTEKAFTVPITDVTENALKDLDDVMKTTKIIIGCFVAITFMAAV
                                        ←───────────────  ──→
                                                         TM 584      590       600       610       620     636
NGL(543)    MLVIFYKMRKQHHRQNHHAPTRTVEIINVDDEITGDTPMESHLPMPAIE----
NAG14(543)  MLIVFYKLRKRHQQRSTVAARTVEIIQVDEDIPAATSAAATAAPSGVSGEGA
HSM(377)    MLVAFYKLRKQHQLHKHHGPTRTVEIINVEDELPAASAVSVAAAAA-------
            ──→
```

FIG. 3B

```
              637         650         660         670       689
NGL(592)   ------HEHLNHYNSYKSPFNHTTTVNTINSIH---SSVHEPLLIRMNSKDNV
NAG14(596) VVLPTIHDHINYNTYKPAHGAHWTENSLGNSLHPTVTTISEPYIIQTHTKDKV
HSM(423)   ----------------------------------------------------
```

```
           690 694
NGL(636)   QETQI
NAG14(649) QETQI
HSM(423)   -----
           ◄──►
           PDZ MOTIF
```

FIG. 3C

```
human NGL      (1) --
MLNKMTLHPQQIMIGPRFNRALFDPLLVVLLALQLLVVAGLVRAQTCP
  mouse NGL    (1) --
MLNKMTLHPQQIMIGPRFNRALFDPLLVVLLALQLLVVAGLVRAQTCP
chicken NGL    (1) ---------------
MIGPRFNRALFDPLLVVLLALQLLVVAGLVRAQTCP
human NAG14    (1) MKLLWQVTVHHH---
TWNAILLPFVYLTAQVWILCAATAAAASAGPQNCP
mouse NAG14    (1) MKLLWQVTVHHH---
TWNAVLLPVVYLTAQVWILCAATAAAASAGPQNCP 51
100
   human NGL   (49)
SVCSCSNQFSKVICVRKNLREVPDGISTNTRLLNLHENQIQIIKVNSFKH
   mouse NGL  (49)
SVCSCSNQFSKVICVRKNLREVPDGISTNTRLLNLHENQIQIIKVNSFKH
chicken NGL   (37)
SVCSCSNQFSKVICVRKNLRDVPDGISTNTRLLNLHENQIQIIKVNSFKH
human NAG14   (48)
SVCSCSNQFSKVVCTRRGLSEVPQGIPSNTRYLNLMENNIQMIQADTFRH
mouse NAG14   (47)
SVCSCSNQFSKVVCTRRGLSEVPQGIPSNTRYLNLMENNIQMIQADTFRH 101
150
   human NGL   (99)
LRHLEILQLSRNHIRTIEIGAFNGLANLNTLELFDNRLTTIPNGAFVYLS
   mouse NGL  (99)
LRHLEILQLSRNHIRTIEIGAFNGLANLNTLELFDNRLTTIPNGAFVYLS
chicken NGL   (87)
LRHLEILQLSRNHIRTIEIGAFNGLANLNTSELFDNRLTTIPNGAFVYLS
human NAG14   (98)
LHHLEVLQLGRNSIRQIEVGAFNGLASLNTLELFDNWLTVIPSGAFEYLS
mouse NAG14   (97)
LHHLEVLQLGRNSIRQIEVGAFNGLASLNTLELFDNWLTVIPSGAFEYLS
```

FIG. 4A

```
                       151
200
   human NGL    (149)
KLKELWLRNNPIESIPSYAFNRIPSLRRLDLGELKRLSYISEGAFEGLSN
   mouse NGL    (149)
KLKELWLRNNPIESIPSYAFNRIPSLRRLDLGELKRLSYISEGAFEGLSN
chicken NGL     (137)   KLKELWLRNNPIESIPSYAFNRIPSLRRLDLGE-------
----------
human NAG14     (148)
KLRELWLRNNPIESIPSYAFNRVPSLMRLDLGELKKLEYISEGAFEGLFN
mouse NAG14     (147)
KLRELWLRNNPIESIPSYAFNRVPSLMRLDLGELKKLEYISEGAFEGLFN 201
250
   human NGL    (199)
LRYLNLAMCNLREIPNLTPLIKLDELDLSGNHLSAIRPGSFQGLMHLQKL
   mouse NGL    (199)
LRYLNLAMCNLREIPNLTPLIKLDELDLSGNHLSAIRPGSFQGLMHLQKL
chicken NGL     (170)   ------------------------------------
----------
human NAG14     (198)
LKYLNLGMCNIKDMPNLTPLVGLEELEMSGNHFPEIRPGSFHGLSSLKKL
mouse NAG14     (197)
LKYLNLGMCNIKDMPNLTPLVGLEELEMSGNHFPEIRPGSFHGLSSLKKL 251
300
   human NGL    (249)
WMIQSQIQVIERNAFDNLQSLVEINLAHNNLTLLPHDLFTPLHHLERTHL
   mouse NGL    (249)
WMIQSQIQVIERNAFDNLQSLVEINLAHNNLTLLPHDLFTPLHHLERTHL
chicken NGL     (170)   ------------------------------------
----------
human NAG14     (248)
WVMNSQVSLIERNAFDGLASLVEINLAHNNLSSLPHDLFTPLRYLVETHL
mouse NAG14     (247)   WVMN-S---
HERNAFDGLASLVEINLAHNNLSSLPHDLFTPLRYLVETHL
```

FIG. 4B

```
                            301
350
   human NGL    (299)
HHNPWNCNCDILWLSWWIKDMAPSNTACCARCNTPPNLKGRYIGELDQNY
   mouse NGL    (299)
HHNPWNCNCDILWLSWWIRDMAPSNTACCARCNTPPNLKGRYIGELDQNY
 chicken NGL    (170) ------------------------------------
----------
human NAG14     (298)
HHNPWNDCDILWLAWWLREYIPINSTCCGRCHAPMHMRGRYLVEVDQAS
mouse NAG14     (293)
HHNPWNDCDILWLAWWLREYIPINSTCCGRCHAPMHMRGRYLVEVDQAA 351
400
   human NGL    (349)
FTCYAPVIVEPPADLNVTEGMAAELKCRASTSLTSVSWITPNGTVMTHGA
   mouse NGL    (349)
FTCYAPVIVEPPADLNVTEGMAAELKCRASTSLTSVSWITPNGTVMTHGA
 chicken NGL    (170) ------------------------------------
----------
human NAG14     (348)  FQCSAPFIMDAPRDLNISEGRMAELKCRTPP-
MSSV WL PNGTVLSHAS
mouse NAG14     (343)  FQCSAPFIMDAPRDLNISEDRMAELKCRTPP-
MSSVKWLLPNGTVLSHAS 401
450
   human NGL    (399)
YKVRIAVLSDGTLNFTNVTVQDTGMYTCMVSNSVGNITASATLNVTAATT YKVRIAVLSDGTLNFTNVTVQDTGMYTCMVSNSVGNITASATLNVTAATT
 chicken NGL    (170) ------------------------------------
----------
human NAG14     (397)
RHPRISVLNDGTLNFSHVLLSDTGVYTCMVINVAGNSNASAYLNVSTAEL
mouse NAG14     (392)
RHPRISVLNDGTLNFSRVLLIDTGVYTCMVINVAGNSNASAYLNVSSAEL
```

FIG. 4C

```
               451
500
  human NGL    (449) TP--
FSYFSTVTVETMEPSQDEARTTDNNVGPTPVVDWETTNVTTSLTPQ
  mouse NGL    (449)
FSYFSTVTVETMEPSQDEARTTDNNVGPTPVIDWETTNVTTSLTPQ
chicken NGL    (170) ------------------------------------
----------
human NAG14    (447)
NTSNYSFFTTVTVETTEISPEDTTRKYKPVPTTSTGYQPAYTTSTTVLIQ
mouse NAG14    (442)
NTPNFSFFTTVTVETTEISPEDITRKYKPVPTTSTGYQPAYTTSTTVLIQ 501
550
  human NGL    (497)
STRSTEKTFTIPVTDINSGIPGIDEVMKTTKIIIGCFVAITLMAAVMLVI
  mouse NGL    (497)
STRSTEKTFTIPVTDINSGIPGIDEVMKTTKIIIGCFVAITLMAAVMLVI
chicken NGL    (170) ------------------------------------
----------
human NAG14    (497)
TTRVPKQVAVPATDTTDKMQTSIDEVMKTTKIIIGCFVAVTLLAAAMLIV
mouse NAG14    (492)
TTRVPKQVPVPSTDTTDKMQTSIDEVMKTTKIIIGCFVAVTLLAAAMLIV 551
600
  human NGL    (547)
FYKMRKQHHRQNHHAPTRTVEIINVDDEITGDTPMESHLPMPAIE-----

FYKMRKQHHRQNHHAPTRTVEIINVDDEITGDTPVESHLPMPAIE-----
chicken NGL    (170) ------------------------------------
----------
human NAG14    (547)
FYKLRKRHQQRSTVTAARTVEIIQVDEDIPAATSAAATAAPSGVSGEGAV
mouse NAG14    (542)
FYKLRKRHQQRSTVTAARTVEIIQVDEDIPAAPAAATAAPSGVSGEGAV
```

FIG. 4D

```
                       601
650
   human NGL    (592) -----HEHLNHYNSYKSPFNHTTTVNTINSIH---
SSVHEPLLIRMNSKD
   mouse NGL    (592) -----HEHLNHYNSYKSPFNHTTTVNTINSIH---
SSVHEPLLIRMNSKD
 chicken NGL    (170) ------------------------------------
----------
human NAG14     (597)
VLPTIHDHINYNTYKPAHGAHWTENSLGNSLHPTVTTISEPYIIQTHTKD
mouse NAG14     (592)
VLPTIHDHINYNTYKPAHGAHWTENSLGNSLHPTVTTISEPYIIQTHTKD 651
   human NGL    (634) NVQETQI
   mouse NGL    (634) NVQETQI
 chicken NGL    (170) -------
                      KVQETQI
mouse NAG14     (642) KVQETQI
```

FIG. 4E

SEQUENCE LISTING

```
<160> NUMBER OF SEQ ID NOS: 8

<210> SEQ ID NO 1
<211> LENGTH: 640
<212> TYPE: PRT
<213> ORGANISM: Homo sapeins

<400> SEQUENCE: 1

Met Leu Asn Lys Met Thr Leu His Pro Gln Gln Ile Met Ile Gly Pro
 1               5                  10                  15

Arg Phe Asn Arg Ala Leu Phe Asp Pro Leu Leu Val Val Leu Leu Ala
             20                  25                  30

Leu Gln Leu Leu Val Val Ala Gly Leu Val Arg Ala Gln Thr Cys Pro
         35                  40                  45

Ser Val Cys Ser Cys Ser Asn Gln Phe Ser Lys Val Ile Cys Val Arg
     50                  55                  60

Lys Asn Leu Arg Glu Val Pro Asp Gly Ile Ser Thr Asn Thr Arg Leu
 65                  70                  75                  80

Leu Asn Leu His Glu Asn Gln Ile Gln Ile Lys Val Asn Ser Phe
                 85                  90                  95

Lys His Leu Arg His Leu Glu Ile Leu Gln Leu Ser Arg Asn His Ile
                100                 105                 110

Arg Thr Ile Glu Ile Gly Ala Phe Asn Gly Leu Ala Asn Leu Asn Thr
            115                 120                 125

Leu Glu Leu Phe Asp Asn Arg Leu Thr Thr Ile Pro Asn Gly Ala Phe
        130                 135                 140

Val Tyr Leu Ser Lys Leu Lys Glu Leu Trp Leu Arg Asn Asn Pro Ile
145                 150                 155                 160

Glu Ser Ile Pro Ser Tyr Ala Phe Asn Arg Ile Pro Ser Leu Arg Arg
                165                 170                 175

Leu Asp Leu Gly Glu Leu Lys Arg Leu Ser Tyr Ile Ser Glu Gly Ala
            180                 185                 190
```

-continued

```
Phe Glu Gly Leu Ser Asn Leu Arg Tyr Leu Asn Leu Ala Met Cys Asn
            195                 200                 205

Leu Arg Glu Ile Pro Asn Leu Thr Pro Leu Ile Lys Leu Asp Glu Leu
210                 215                 220

Asp Leu Ser Gly Asn His Leu Ser Ala Ile Arg Pro Gly Ser Phe Gln
225                 230                 235                 240

Gly Leu Met His Leu Gln Lys Leu Trp Met Ile Gln Ser Gln Ile Gln
                245                 250                 255

Val Ile Glu Arg Asn Ala Phe Asp Asn Leu Gln Ser Leu Val Glu Ile
            260                 265                 270

Asn Leu Ala His Asn Asn Leu Thr Leu Leu Pro His Asp Leu Phe Thr
            275                 280                 285

Pro Leu His His Leu Glu Arg Ile His Leu His Asn Pro Trp Asn
290                 295                 300

Cys Asn Cys Asp Ile Leu Trp Leu Ser Trp Trp Ile Lys Asp Met Ala
305                 310                 315                 320

Pro Ser Asn Thr Ala Cys Cys Ala Arg Cys Asn Thr Pro Pro Asn Leu
                325                 330                 335

Lys Gly Arg Tyr Ile Gly Glu Leu Asp Gln Asn Tyr Phe Thr Cys Tyr
            340                 345                 350

Ala Pro Val Ile Val Glu Pro Pro Ala Asp Leu Asn Val Thr Glu Gly
            355                 360                 365

Met Ala Ala Glu Leu Lys Cys Arg Ala Ser Thr Ser Leu Thr Ser Val
    370                 375                 380

Ser Trp Ile Thr Pro Asn Gly Thr Val Met Thr His Gly Ala Tyr Lys
385                 390                 395                 400

Val Arg Ile Ala Val Leu Ser Asp Gly Thr Leu Asn Phe Thr Asn Val
                405                 410                 415

Thr Val Gln Asp Thr Gly Met Tyr Thr Cys Met Val Ser Asn Ser Val
            420                 425                 430

Gly Asn Thr Thr Ala Ser Ala Thr Leu Asn Val Thr Ala Ala Thr Thr
            435                 440                 445

Thr Pro Phe Ser Tyr Phe Ser Thr Val Thr Val Glu Thr Met Glu Pro
    450                 455                 460

Ser Gln Asp Glu Ala Arg Thr Thr Asp Asn Asn Val Gly Pro Thr Pro
465                 470                 475                 480

Val Val Asp Trp Glu Thr Thr Asn Val Thr Thr Ser Leu Thr Pro Gln
                485                 490                 495

Ser Thr Arg Ser Thr Glu Lys Thr Phe Thr Ile Pro Val Thr Asp Ile
            500                 505                 510

Asn Ser Gly Ile Pro Gly Ile Asp Glu Val Met Lys Thr Thr Lys Ile
            515                 520                 525

Ile Ile Gly Cys Phe Val Ala Ile Thr Leu Met Ala Ala Val Met Leu
    530                 535                 540

Val Ile Phe Tyr Lys Met Arg Lys Gln His His Arg Gln Asn His His
545                 550                 555                 560

Ala Pro Thr Arg Thr Val Glu Ile Ile Asn Val Asp Asp Glu Ile Thr
                565                 570                 575

Gly Asp Thr Pro Met Glu Ser His Leu Pro Met Pro Ala Ile Glu His
            580                 585                 590

Glu His Leu Asn His Tyr Asn Ser Tyr Lys Ser Pro Phe Asn His Thr
            595                 600                 605

Thr Thr Val Asn Thr Ile Asn Ser Ile His Ser Ser Val His Glu Pro
```

Leu Leu Ile Arg Met Asn Ser Lys Asp Asn Val Gln Glu Thr Gln Ile
625                 630                 635                 640

<210> SEQ ID NO 2
<211> LENGTH: 653
<212> TYPE: PRT
<213> ORGANISM: Homo sapiens

<400> SEQUENCE: 2

Met Lys Leu Leu Trp Gln Val Thr Val His His Thr Trp Asn Ala
1               5                   10                  15

Ile Leu Leu Pro Phe Val Tyr Leu Thr Ala Gln Val Trp Ile Leu Cys
                20                  25                  30

Ala Ala Ile Ala Ala Ala Ala Ser Ala Gly Pro Gln Asn Cys Pro Ser
            35                  40                  45

Val Cys Ser Cys Ser Asn Gln Phe Ser Lys Val Val Cys Thr Arg Arg
        50                  55                  60

Gly Leu Ser Glu Val Pro Gln Gly Ile Pro Ser Asn Thr Arg Tyr Leu
65                  70                  75                  80

Asn Leu Met Glu Asn Asn Ile Gln Met Ile Gln Ala Asp Thr Phe Arg
                85                  90                  95

His Leu His His Leu Glu Val Leu Gln Leu Gly Arg Asn Ser Ile Arg
            100                 105                 110

Gln Ile Glu Val Gly Ala Phe Asn Gly Leu Ala Ser Leu Asn Thr Leu
        115                 120                 125

Glu Leu Phe Asp Asn Trp Leu Thr Val Ile Pro Ser Gly Ala Phe Glu
130                 135                 140

Tyr Leu Ser Lys Leu Arg Glu Leu Trp Leu Arg Asn Asn Pro Ile Glu
145                 150                 155                 160

Ser Ile Pro Ser Tyr Ala Phe Asn Arg Val Pro Ser Leu Met Arg Leu
                165                 170                 175

Asp Leu Gly Glu Leu Lys Lys Leu Glu Tyr Ile Ser Glu Gly Ala Phe
            180                 185                 190

Glu Gly Leu Phe Asn Leu Lys Tyr Leu Asn Leu Gly Met Cys Asn Ile
        195                 200                 205

Lys Asp Met Pro Asn Leu Thr Pro Leu Val Gly Leu Glu Glu Leu Glu
210                 215                 220

Met Ser Gly Asn His Phe Pro Glu Ile Arg Pro Gly Ser Phe His Gly
225                 230                 235                 240

Leu Ser Ser Leu Lys Lys Leu Trp Val Met Asn Ser Gln Val Ser Leu
                245                 250                 255

Ile Glu Arg Asn Ala Phe Asp Gly Leu Ala Ser Leu Val Glu Leu Asn
            260                 265                 270

Leu Ala His Asn Asn Leu Ser Ser Leu Pro His Asp Leu Phe Thr Pro
        275                 280                 285

Leu Arg Tyr Leu Val Glu Leu His Leu His His Asn Pro Trp Asn Cys
290                 295                 300

Asp Cys Asp Ile Leu Trp Leu Ala Trp Trp Leu Arg Glu Tyr Ile Pro
305                 310                 315                 320

Thr Asn Ser Thr Cys Cys Gly Arg Cys His Ala Pro Met His Met Arg
                325                 330                 335

Gly Arg Tyr Leu Val Glu Val Asp Gln Ala Ser Phe Gln Cys Ser Ala
            340                 345                 350

```
Pro Phe Ile Met Asp Ala Pro Arg Asp Leu Asn Ile Ser Glu Gly Arg
        355                 360                 365

Met Ala Glu Leu Lys Cys Arg Thr Pro Pro Met Ser Ser Val Lys Trp
    370                 375                 380

Leu Leu Pro Asn Gly Thr Val Leu Ser His Ala Ser Arg His Pro Arg
385                 390                 395                 400

Ile Ser Val Leu Asn Asp Gly Thr Leu Asn Phe Ser His Val Leu Leu
                405                 410                 415

Ser Asp Thr Gly Val Tyr Thr Cys Met Val Thr Asn Val Ala Gly Asn
            420                 425                 430

Ser Asn Ala Ser Ala Tyr Leu Asn Val Ser Thr Ala Glu Leu Asn Thr
        435                 440                 445

Ser Asn Tyr Ser Phe Phe Thr Thr Val Thr Val Glu Thr Thr Glu Ile
    450                 455                 460

Ser Pro Glu Asp Thr Thr Arg Lys Tyr Lys Pro Val Pro Thr Thr Ser
465                 470                 475                 480

Thr Gly Tyr Gln Pro Ala Tyr Thr Thr Ser Thr Thr Val Leu Ile Gln
                485                 490                 495

Thr Thr Arg Val Pro Lys Gln Val Ala Val Pro Ala Thr Asp Thr Thr
            500                 505                 510

Asp Lys Met Gln Thr Ser Leu Asp Glu Val Met Lys Thr Thr Lys Ile
        515                 520                 525

Ile Ile Gly Cys Phe Val Ala Val Thr Leu Leu Ala Ala Ala Met Leu
    530                 535                 540

Ile Val Phe Tyr Lys Leu Arg Lys Arg His Gln Gln Arg Ser Thr Val
545                 550                 555                 560

Thr Ala Ala Arg Thr Val Glu Ile Ile Gln Val Asp Glu Asp Ile Pro
                565                 570                 575

Ala Ala Thr Ser Ala Ala Ala Thr Ala Ala Pro Ser Gly Val Ser Gly
            580                 585                 590

Glu Gly Ala Val Val Leu Pro Thr Ile His Asp His Ile Asn Tyr Asn
        595                 600                 605

Thr Tyr Lys Pro Ala His Gly Ala His Trp Thr Glu Asn Ser Leu Gly
    610                 615                 620

Asn Ser Leu His Pro Thr Val Thr Thr Ile Ser Glu Pro Tyr Ile Ile
625                 630                 635                 640

Gln Thr His Thr Lys Asp Lys Val Gln Glu Thr Gln Ile
                645                 650

<210> SEQ ID NO 3
<211> LENGTH: 422
<212> TYPE: PRT
<213> ORGANISM: Homo sapiens

<400> SEQUENCE: 3

Met Cys Asn Leu Lys Asp Ile Pro Asn Leu Thr Ala Leu Val Arg Leu
  1               5                  10                  15

Glu Glu Leu Glu Leu Ser Gly Asn Arg Leu Asp Leu Ile Arg Pro Gly
            20                  25                  30

Ser Phe Gln Gly Leu Thr Ser Leu Arg Lys Leu Trp Leu Met His Ala
        35                  40                  45

Gln Val Ala Thr Ile Glu Arg Asn Ala Phe Asp Asp Leu Lys Ser Leu
    50                  55                  60

Glu Glu Leu Asn Leu Ser His Asn Asn Leu Met Ser Leu Pro His Asp
65                  70                  75                  80
```

```
Leu Phe Thr Pro Leu His Arg Leu Glu Arg Val His Leu Asn His Asn
                85                  90                  95

Pro Trp His Cys Asn Cys Asp Val Leu Trp Leu Ser Trp Trp Leu Lys
            100                 105                 110

Glu Thr Val Pro Ser Asn Thr Thr Cys Cys Ala Arg Cys His Ala Pro
        115                 120                 125

Ala Gly Leu Lys Gly Arg Tyr Ile Gly Glu Leu Asp Gln Ser His Phe
    130                 135                 140

Thr Cys Tyr Ala Pro Val Ile Val Glu Pro Thr Asp Leu Asn Val
145                 150                 155                 160

Thr Glu Gly Met Ala Ala Glu Leu Lys Cys Arg Thr Gly Thr Ser Met
                165                 170                 175

Thr Ser Val Asn Trp Leu Thr Pro Asn Gly Thr Leu Met Thr His Gly
            180                 185                 190

Ser Tyr Arg Val Arg Ile Ser Val Leu His Asp Gly Thr Leu Asn Phe
        195                 200                 205

Thr Asn Val Thr Val Gln Asp Thr Gly Gln Tyr Thr Cys Met Val Thr
    210                 215                 220

Asn Ser Ala Gly Asn Thr Thr Ala Ser Ala Thr Leu Asn Val Ser Ala
225                 230                 235                 240

Val Asp Pro Val Ala Ala Gly Thr Gly Ser Gly Gly Gly Pro
                245                 250                 255

Gly Gly Ser Gly Gly Val Gly Gly Ser Gly Gly Tyr Thr Tyr Phe
            260                 265                 270

Thr Thr Val Thr Val Glu Thr Leu Glu Thr Gln Pro Gly Glu Glu Ala
        275                 280                 285

Leu Gln Pro Arg Gly Thr Glu Lys Glu Pro Pro Gly Pro Thr Thr Asp
    290                 295                 300

Gly Val Trp Gly Gly Arg Pro Gly Asp Ala Ala Gly Pro Ala Ser
305                 310                 315                 320

Ser Ser Thr Thr Ala Pro Ala Pro Arg Ser Ser Arg Pro Thr Glu Lys
                325                 330                 335

Ala Phe Thr Val Pro Ile Thr Asp Val Thr Glu Asn Ala Leu Lys Asp
            340                 345                 350

Leu Asp Asp Val Met Lys Thr Thr Lys Ile Ile Gly Cys Phe Val
        355                 360                 365

Ala Ile Thr Phe Met Ala Ala Val Met Leu Val Ala Phe Tyr Lys Leu
    370                 375                 380

Arg Lys Gln His Gln Leu His Lys His His Gly Pro Thr Arg Thr Val
385                 390                 395                 400

Glu Ile Ile Asn Val Glu Asp Glu Leu Pro Ala Ala Ser Ala Val Ser
                405                 410                 415

Val Ala Ala Ala Ala Ala
            420

<210> SEQ ID NO 4
<211> LENGTH: 640
<212> TYPE: PRT
<213> ORGANISM: Mus musculus

<400> SEQUENCE: 4

Met Leu Asn Lys Met Thr Leu His Pro Gln Gln Ile Met Ile Gly Pro
1               5                   10                  15

Arg Phe Asn Arg Ala Leu Phe Asp Pro Leu Leu Val Val Leu Leu Ala
```

-continued

```
            20                  25                  30
Leu Gln Leu Leu Val Val Ala Gly Leu Val Arg Ala Gln Thr Cys Pro
            35                  40                  45

Ser Val Cys Ser Cys Ser Asn Gln Phe Ser Lys Val Ile Cys Val Arg
 50                  55                  60

Lys Asn Leu Arg Glu Val Pro Asp Gly Ile Ser Thr Asn Thr Arg Leu
 65                  70                  75                  80

Leu Asn Leu His Glu Asn Gln Ile Gln Ile Ile Lys Val Asn Ser Phe
                85                  90                  95

Lys His Leu Arg His Leu Glu Ile Leu Gln Leu Ser Arg Asn His Ile
                100                 105                 110

Arg Thr Ile Glu Ile Gly Ala Phe Asn Gly Leu Ala Asn Leu Asn Thr
                115                 120                 125

Leu Glu Leu Phe Asp Asn Arg Leu Thr Thr Ile Pro Asn Gly Ala Phe
                130                 135                 140

Val Tyr Leu Ser Lys Leu Lys Glu Leu Trp Leu Arg Asn Asn Pro Ile
145                 150                 155                 160

Glu Ser Ile Pro Ser Tyr Ala Phe Asn Arg Ile Pro Ser Leu Arg Arg
                165                 170                 175

Leu Asp Leu Gly Glu Leu Lys Arg Leu Ser Tyr Ile Ser Glu Gly Ala
                180                 185                 190

Phe Glu Gly Leu Ser Asn Leu Arg Tyr Leu Asn Leu Ala Met Cys Asn
                195                 200                 205

Leu Arg Glu Ile Pro Asn Leu Thr Pro Leu Ile Lys Leu Asp Glu Leu
                210                 215                 220

Asp Leu Ser Gly Asn His Leu Ser Ala Ile Arg Pro Gly Ser Phe Gln
225                 230                 235                 240

Gly Leu Met His Leu Gln Lys Leu Trp Met Ile Gln Ser Gln Ile Gln
                245                 250                 255

Val Ile Glu Arg Asn Ala Phe Asp Asn Leu Gln Ser Leu Val Glu Ile
                260                 265                 270

Asn Leu Ala His Asn Asn Leu Thr Leu Leu Pro His Asp Leu Phe Thr
                275                 280                 285

Pro Leu His His Leu Glu Arg Ile His Leu His Asn Pro Trp Asn
290                 295                 300

Cys Asn Cys Asp Ile Leu Trp Leu Ser Trp Trp Ile Arg Asp Met Ala
305                 310                 315                 320

Pro Ser Asn Thr Ala Cys Cys Ala Arg Cys Asn Thr Pro Pro Asn Leu
                325                 330                 335

Lys Gly Arg Tyr Ile Gly Glu Leu Asp Gln Asn Tyr Phe Thr Cys Tyr
                340                 345                 350

Ala Pro Val Ile Val Glu Pro Pro Ala Asp Leu Asn Val Thr Glu Gly
                355                 360                 365

Met Ala Ala Glu Leu Lys Cys Arg Ala Ser Thr Ser Leu Thr Ser Val
                370                 375                 380

Ser Trp Ile Thr Pro Asn Gly Thr Val Met Thr His Gly Ala Tyr Lys
385                 390                 395                 400

Val Arg Ile Ala Val Leu Ser Asp Gly Thr Leu Asn Phe Thr Asn Val
                405                 410                 415

Thr Val Gln Asp Thr Gly Met Tyr Thr Cys Met Val Ser Asn Ser Val
                420                 425                 430

Gly Asn Thr Thr Ala Ser Ala Thr Leu Asn Val Thr Ala Ala Thr Thr
                435                 440                 445
```

```
Thr Pro Phe Ser Tyr Phe Ser Thr Val Thr Val Glu Thr Met Glu Pro
    450                 455                 460

Ser Gln Asp Glu Ala Arg Thr Thr Asp Asn Asn Val Gly Pro Thr Pro
465                 470                 475                 480

Val Ile Asp Trp Glu Thr Thr Asn Val Thr Thr Ser Leu Thr Pro Gln
                485                 490                 495

Ser Thr Arg Ser Thr Glu Lys Thr Phe Thr Ile Pro Val Thr Asp Ile
            500                 505                 510

Asn Ser Gly Ile Pro Gly Ile Asp Glu Val Met Lys Thr Thr Lys Ile
        515                 520                 525

Ile Ile Gly Cys Phe Val Ala Ile Thr Leu Met Ala Ala Val Met Leu
    530                 535                 540

Val Ile Phe Tyr Lys Met Arg Lys Gln His His Arg Gln Asn His His
545                 550                 555                 560

Ala Pro Thr Arg Thr Val Glu Ile Ile Asn Val Asp Asp Glu Ile Thr
                565                 570                 575

Gly Asp Thr Pro Val Glu Ser His Leu Pro Met Pro Ala Ile Glu His
            580                 585                 590

Glu His Leu Asn His Tyr Asn Ser Tyr Lys Ser Pro Phe Asn His Thr
        595                 600                 605

Thr Thr Val Asn Thr Ile Asn Ser Ile His Ser Ser Val His Glu Pro
    610                 615                 620

Leu Leu Ile Arg Met Asn Ser Lys Asp Asn Val Gln Glu Thr Gln Ile
625                 630                 635                 640

<210> SEQ ID NO 5
<211> LENGTH: 169
<212> TYPE: PRT
<213> ORGANISM: chicken

<400> SEQUENCE: 5

Met Ile Gly Pro Arg Phe Asn Arg Ala Leu Phe Asp Pro Leu Leu Val
1               5                   10                  15

Val Leu Leu Ala Leu Gln Leu Leu Val Val Ala Gly Leu Val Arg Ala
                20                  25                  30

Gln Thr Cys Pro Ser Val Cys Ser Cys Ser Asn Gln Phe Ser Lys Val
            35                  40                  45

Ile Cys Val Arg Lys Asn Leu Arg Asp Val Pro Asp Gly Ile Ser Thr
        50                  55                  60

Asn Thr Arg Leu Leu Asn Leu His Glu Asn Gln Ile Gln Ile Ile Lys
65                  70                  75                  80

Val Asn Ser Phe Lys His Leu Arg His Leu Glu Ile Leu Gln Leu Ser
                85                  90                  95

Arg Asn His Ile Arg Thr Ile Glu Ile Gly Ala Phe Asn Gly Leu Ala
            100                 105                 110

Asn Leu Asn Thr Ser Glu Leu Phe Asp Asn Arg Leu Thr Thr Ile Pro
        115                 120                 125

Asn Gly Ala Phe Val Tyr Leu Ser Lys Leu Lys Glu Leu Trp Leu Arg
    130                 135                 140

Asn Asn Pro Ile Glu Ser Ile Pro Ser Tyr Ala Phe Asn Arg Ile Pro
145                 150                 155                 160

Ser Leu Arg Arg Leu Asp Leu Gly Glu
                165
```

<210> SEQ ID NO 6
<211> LENGTH: 648
<212> TYPE: PRT
<213> ORGANISM: Mus musculus

<400> SEQUENCE: 6

Met Lys Leu Leu Trp Gln Val Thr Val His Thr Trp Asn Ala Val
1               5                   10                  15

Leu Leu Pro Val Val Tyr Leu Thr Ala Gln Val Trp Ile Leu Cys Ala
            20                  25                  30

Ala Ile Ala Ala Ala Ala Ser Ala Gly Pro Gln Asn Cys Pro Ser Val
        35                  40                  45

Cys Ser Cys Ser Asn Gln Phe Ser Lys Val Val Cys Thr Arg Arg Gly
    50                  55                  60

Leu Ser Glu Val Pro Gln Gly Ile Pro Ser Asn Thr Arg Tyr Leu Asn
65                  70                  75                  80

Leu Met Glu Asn Asn Ile Gln Met Ile Gln Ala Asp Thr Phe Arg His
                85                  90                  95

Leu His His Leu Glu Val Leu Gln Leu Gly Arg Asn Ser Ile Arg Gln
            100                 105                 110

Ile Glu Val Gly Ala Phe Asn Gly Leu Ala Ser Leu Asn Thr Leu Glu
        115                 120                 125

Leu Phe Asp Asn Trp Leu Thr Val Ile Pro Ser Gly Ala Phe Glu Tyr
    130                 135                 140

Leu Ser Lys Leu Arg Glu Leu Trp Leu Arg Asn Asn Pro Ile Glu Ser
145                 150                 155                 160

Ile Pro Ser Tyr Ala Phe Asn Arg Val Pro Ser Leu Met Arg Leu Asp
                165                 170                 175

Leu Gly Glu Leu Lys Lys Leu Glu Tyr Ile Ser Glu Gly Ala Phe Glu
            180                 185                 190

Gly Leu Phe Asn Leu Lys Tyr Leu Asn Leu Gly Met Cys Asn Ile Lys
        195                 200                 205

Asp Met Pro Asn Leu Thr Pro Leu Val Gly Leu Glu Glu Leu Glu Met
    210                 215                 220

Ser Gly Asn His Phe Pro Glu Ile Arg Pro Gly Ser Phe His Gly Leu
225                 230                 235                 240

Ser Ser Leu Lys Lys Leu Trp Val Met Asn Ser His Glu Arg Asn Ala
                245                 250                 255

Phe Asp Gly Leu Ala Ser Leu Val Glu Leu Asn Leu Ala His Asn Asn
            260                 265                 270

Leu Ser Ser Leu Pro His Asp Leu Phe Thr Pro Leu Arg Tyr Leu Val
        275                 280                 285

Glu Leu His Leu His His Asn Pro Trp Asn Cys Asp Cys Asp Ile Leu
    290                 295                 300

Trp Leu Ala Trp Trp Leu Arg Glu Tyr Ile Pro Thr Asn Ser Thr Cys
305                 310                 315                 320

Cys Gly Arg Cys His Ala Pro Met His Met Arg Gly Arg Tyr Leu Val
                325                 330                 335

Glu Val Asp Gln Ala Ala Phe Gln Cys Ser Ala Pro Phe Ile Met Asp
            340                 345                 350

Ala Pro Arg Asp Leu Asn Ile Ser Glu Asp Arg Met Ala Glu Leu Lys
        355                 360                 365

Cys Arg Thr Pro Pro Met Ser Ser Val Lys Trp Leu Leu Pro Asn Gly
    370                 375                 380

-continued

```
Thr Val Leu Ser His Ala Ser Arg His Pro Arg Ile Ser Val Leu Asn
385                 390                 395                 400

Asp Gly Thr Leu Asn Phe Ser Arg Val Leu Leu Ile Asp Thr Gly Val
            405                 410                 415

Tyr Thr Cys Met Val Thr Asn Val Ala Gly Asn Ser Asn Ala Ser Ala
        420                 425                 430

Tyr Leu Asn Val Ser Ser Ala Glu Leu Asn Thr Pro Asn Phe Ser Phe
    435                 440                 445

Phe Thr Thr Val Thr Val Glu Thr Thr Glu Ile Ser Pro Glu Asp Ile
450                 455                 460

Thr Arg Lys Tyr Lys Pro Val Pro Thr Thr Ser Thr Gly Tyr Gln Pro
465                 470                 475                 480

Ala Tyr Thr Thr Ser Thr Thr Val Leu Ile Gln Thr Thr Arg Val Pro
                485                 490                 495

Lys Gln Val Pro Val Pro Ser Thr Asp Thr Thr Asp Lys Met Gln Thr
            500                 505                 510

Ser Leu Asp Glu Val Met Lys Thr Thr Lys Ile Ile Ile Gly Cys Phe
        515                 520                 525

Val Ala Val Thr Leu Leu Ala Ala Ala Met Leu Ile Val Phe Tyr Lys
    530                 535                 540

Leu Arg Lys Arg His Gln Gln Arg Ser Thr Val Thr Ala Ala Arg Thr
545                 550                 555                 560

Val Glu Ile Ile Gln Val Asp Glu Asp Ile Pro Ala Ala Ala Pro Ala
                565                 570                 575

Ala Ala Thr Ala Ala Pro Ser Gly Val Ser Gly Glu Gly Ala Val Val
            580                 585                 590

Leu Pro Thr Ile His Asp His Ile Asn Tyr Asn Thr Tyr Lys Pro Ala
        595                 600                 605

His Gly Ala His Trp Thr Glu Asn Ser Leu Gly Asn Ser Leu His Pro
    610                 615                 620

Thr Val Thr Thr Ile Ser Glu Pro Tyr Ile Ile Gln Thr His Thr Lys
625                 630                 635                 640

Asp Lys Val Gln Glu Thr Gln Ile
                645

<210> SEQ ID NO 7
<211> LENGTH: 6
<212> TYPE: PRT
<213> ORGANISM: Artificial Sequence
<220> FEATURE:
<223> OTHER INFORMATION: PDZ domain-binding motif

<400> SEQUENCE: 7

Val Gln Glu Thr Gln Ile
 1               5

<210> SEQ ID NO 8
<211> LENGTH: 4
<212> TYPE: PRT
<213> ORGANISM: Artificial Sequence
<220> FEATURE:
<223> OTHER INFORMATION: Human Netrin-G1

<400> SEQUENCE: 8

Glu Thr Gln Ile
 1
```

PROMOTION OF AXONAL REGENERATION

BACKGROUND OF THE INVENTION

1. Field of the Invention

The present invention concerns a method of promoting axonal regeneration. In particular, the invention concerns a method of promoting the growth or regeneration of neurons, and treating disease or conditions associated with the loss, loss of function or dysfunction of nerve cells, in particular thalamic nerve cells, by administering a polypeptide having a high degree of sequence identity with a native sequence Netrin G1 (NGL-1) or an agonist thereof.

2. Description of the Related Art

The Netrins are a family of laminin-related, diffusible axon guidance molecules that are conserved from C. elegans to vertebrates [Ishii, N., Wadsworth, W. G., Stern, B. D., Culotti, J. G. & Hedgecock, E. M. "UNC-6, a laminin-related protein, guides cell and pioneer axon migrations in C. elegans". Neuron 9, 873-881. (1992); Serafini, T. et al. "The netrins define a family of axon outgrowth-promoting proteins homologous to C. elegans UNC-6", Cell 78, 409-424. (1994)] The vertebrate netrins are highly expressed in the ventral midline of the central nervous system (CNS), attracting the commissural axons and repelling the trochlear motor axons [Ishii, N., Wadsworth, W. G., Stern, B. D., Culotti, J. G. & Hedgecock, E. M. "UNC-6, a laminin-related protein, guides cell and pioneer axon migrations in C. elegans". Neuron 9, 873-881. (1992)]. Axonal attraction to Netrins is mediated mainly by the transmembrane receptor DCC, whereas its repulsive action is dependent on both the DCC and Unc5 receptors [Hedgecock, E. M., Culotti, J. G. & Hall, D. H. "The unc-5, unc-6, and unc-40 genes guide circumferential migrations of pioneer axons and mesodermal cells on the epidermis in C. elegans", Neuron 4, 61-85. (1990); Hamelin, M., Zhou, Y., Su, M. W., Scott, I. M. & Culotti, J. G. "Expression of the UNC-5 guidance receptor in the touch neurons of C. elegans steers their axons dorsally", Nature 364, 327-330. (1993); Keino-Masu, K. et al. "Deleted in Colorectal Cancer (DCC) encodes a netrin receptor", Cell 87, 175-185. (1996); Leonardo, E. D. et al. "Vertebrate homologues of C. elegans UNC-5 are candidate netrin receptors", Nature 386, 833-838. (1997)].

Recently a Netrin-related molecule, Netrin-G1 (also named as Laminet-1), was identified and shown to be distinguished from the classical netrins in a number of aspects [Nakashiba, T. et al. "Netrin-G1: a novel glycosyl phosphatidylinositol-linked mammalian netrin that is functionally divergent from classical netrins" J. Neurosci. 20, 6540-6550. (2000); Yin, Y., Miner, J. H. & Sanes, J. R. "Laminets: laminin- and netrin-related genes expressed in distinct neuronal subsets", Mol. Cell. Neurosci. 19, 344-358. (2002)]. See also, WO 99/63088, published Dec. 9, 1999, disclosing the sequence of Netrin-G1 (originally designated PRO1133, encoded by DNA53913), and WO 01/68848, published Sep. 20, 2001, including microarray data demonstrating the over-expression of Netrin-G1 (PRO1133) in tumor.

Unlike other Netrins, Netrin-G1 is predominantly tethered to the cell membrane via a C-terminal glycosyl-phosphatidylinositol (GPI) anchor and is not expressed in the ventral midline of the CNS. Instead it is found in sets of projection neurons such as the mitral cells of the olfactory bulb, the deep cerebellar nuclei and the dorsal thalamus. Multiple splice variants of Netrin-G1 have been uncovered, suggesting potential complexity of this gene. More importantly, none of the multiple isoforms of Netrin-G1 binds DCC or Unc5, the identified netrin receptors [Nakashiba, T. et al. "Netrin-G1: a novel glycosyl phosphatidylinositol-linked mammalian netrin that is functionally divergent from classical netrins", J. Neurosci. 20, 6540-6550. (2000)]. Therefore its function and mode of action were not known.

The thalamocortical axons (TCAs) project from the dorsal thalamus to the cerebral cortex. These axons first extend toward the ventral thalamus and then turn 90° rostrally, coursing through the ventral telencephalon (i.e. subpallium/the striatum) within the internal capsule and they turn dorsally to reach their final target, the cerebral cortex. Along this complex trajectory, both attractive and repulsive signals guide the thalamocortical axons [Braisted, J. E., Tuttle, R. & O'Leary D, D. "Thalamocortical axons are influenced by chemorepellent and chemoattractant activities localized to decision points along their path", Dev. Biol. (Orlando) 208, 430-440 (1999)]. Specifically, the repulsive signals Slit-1 and Slit-2 are required to steer the thalamocortical axons away from the ventral midline region of the diencephalons [Bagri, A. et al. "Slit proteins prevent midline crossing and determine the dorsoventral position of major axonal pathways in the mammalian forebrain", Neuron 33, 233-248. (2002)], while Netrin-1 expressed in the ventral telencephalon appear to attract the thalamocortical axons into the internal capsule [Braisted, J. E. et al. "Netrin-1 promotes thalamic axon growth and is required for proper development of the thalamocortical projection," J. Neurosci 20, 5792-5801 (2000)]. However, a substantial population of the thalamocortical axons is still able to reach the internal capsule and the cerebral cortex in the Netrin1-deficient mice [Bagri, A. et al. "Slit proteins prevent midline crossing and determine the dorsoventral position of major axonal pathways in the mammalian forebrain." Neuron 33, 233-248. (2002)] suggesting that additional attractive factor(s) must be involved.

A leucine-rich repeat containing polypeptide designated PRO331 (encoded by DNA40981), was disclosed in WO 99/142328, published Mar. 25, 1999 and WO 00/15796, published Mar. 23, 2000, and shown to inhibit VEGF-stimulated proliferation of endothelial cell growth. WO 01/04311, published Jan. 18, 2001 disclosed results demonstrating that the same molecule has pro-inflammatory properties.

In Example 171 of WO 00/73454, published Dec. 7, 2000, PRO331 was shown to bind PRO1133 (now named Netrin-G1) and vice versa.

SUMMARY OF THE INVENTION

The present invention is, at least part, based on experimental data demonstrating that a human polypeptide, originally designated PRO331, and hereinafter termed Netrin-G1 Ligand, or NGL-1, not only binds to but is a functional ligand of polypeptide PRO1133 (hereafter referred to as Netrin-G1), and that this receptor-ligand pair plays an important role in neural regeneration and axon outgrowth.

In one aspect, the invention concerns a method of promoting axonal growth or regeneration comprising delivering to an injured neuron an effective amount of a polypeptide having at least about 80% sequence identity with amino acid residues 44-352 of SEQ ID NO: 1 and comprising a transmembrane region, or an agonist thereof.

In particular embodiments, the polypeptide has at least about 85%, or at least about 90%, or at least about 95%, or at least about 98% or at least about 99% sequence identity with amino acid residues 44-352 of SEQ ID NO: 1.

In another embodiment, the polypeptide further comprises a C-terminal PDZ domain-binding motif, where the PDZ domain-binding motif may, for example, have the sequence of VQETQI (SEQ ID NO: 7).

In yet another embodiment, the polypeptide comprises an extracellular domain (ECD) comprising nine leucine-rich repeats (LRRs), and may further comprise an N-terminal signal sequence.

In a further embodiment, the polypeptide comprises amino acids 44-352 of SEQ ID NO: 1.

In a still further embodiment, the polypeptide comprises amino acids 44-428 of SEQ ID NO: 1.

In an additional embodiment, the polypeptide comprises amino acids 44-546 of SEQ ID NO: 1.

The polypeptide employed in the foregoing method may preferably be human NGL-1 (SEQ ID NO: 1), with or without the N-terminal signal sequence and with or without an immunoglobulin-like region, or a non-human homologue of human NGL-1 (SEQ ID NO: 1), with or without an N-terminal signal sequence and with or without an immunoglobulin-like region. In specific embodiments, the non-human homologue can be mouse NGL-1 (SEQ ID NO: 4), or chicken NLG-1 (SEQ ID NO: 5).

The NGL-1 agonist can, for example, be an agonist antibody, including antibody fragments, or a small molecule, including small organic molecules and peptides.

In another aspect, the invention concerns a method for treating a disease or condition associated with the loss, loss of function or dysfunction of nerve cells comprising delivering to said nerve cells an effective amount of a polypeptide having at least 80% sequence identity with amino acid residues 44-352 of SEQ ID NO: 1 and comprising a transmembrane region, or an agonist thereof.

In a particular embodiment, the nerve cells are thalamic nerve cells.

In another embodiment, the disease or condition is a neurodegenerative disease.

In a further embodiment, the disease or condition is characterized by nerve cell injury, where the injury may, for example, be due to mechanical trauma, or associated with diabetes, stroke, liver or kidney dysfunction, other endocrine or metabolic derangements, chemotherapy or radiation, or chemical intoxication of the nervous system, or spinal cord injury. Thus, the disease or condition may be allodynia or pain following spinal cord injury.

In another embodiment, the disease or condition is associated with neural dysfunction, and can, for example, be selected from the group consisting of Alzheimer's disease, Parkinson's disease, Huntington's chorea, amylotrophic lateral sclerosis (ALS), and peripheral neuropathies.

In another embodiment, the disease or condition is a congenital or hereditary abnormality, such as a Charcot-Marie-Tooth disease.

In yet another embodiment, the disease or condition is an autoimmune disease attacking axons of the central or peripheral nervous system, such as multiple sclerosis or Gulliam-Barre syndrome.

In a further aspect, the invention concerns a method for treating a disease or condition associated with the loss, loss of function or dysfunction of nerve cells comprising delivering to said nerve cells an effective amount of a nucleic acid encoding a polypeptide having at least 80% sequence identity with amino acid residues 44-352 of SEQ ID NO: 1 and comprising a transmembrane region, or a peptide or polypeptide agonist thereof. In a preferred embodiment, the nerve cells are thalamic nerve cells. All embodiment discussed above in connection with other aspects of the invention are also embodiments of the present method, and are within the scope of the invention.

Figure 1:
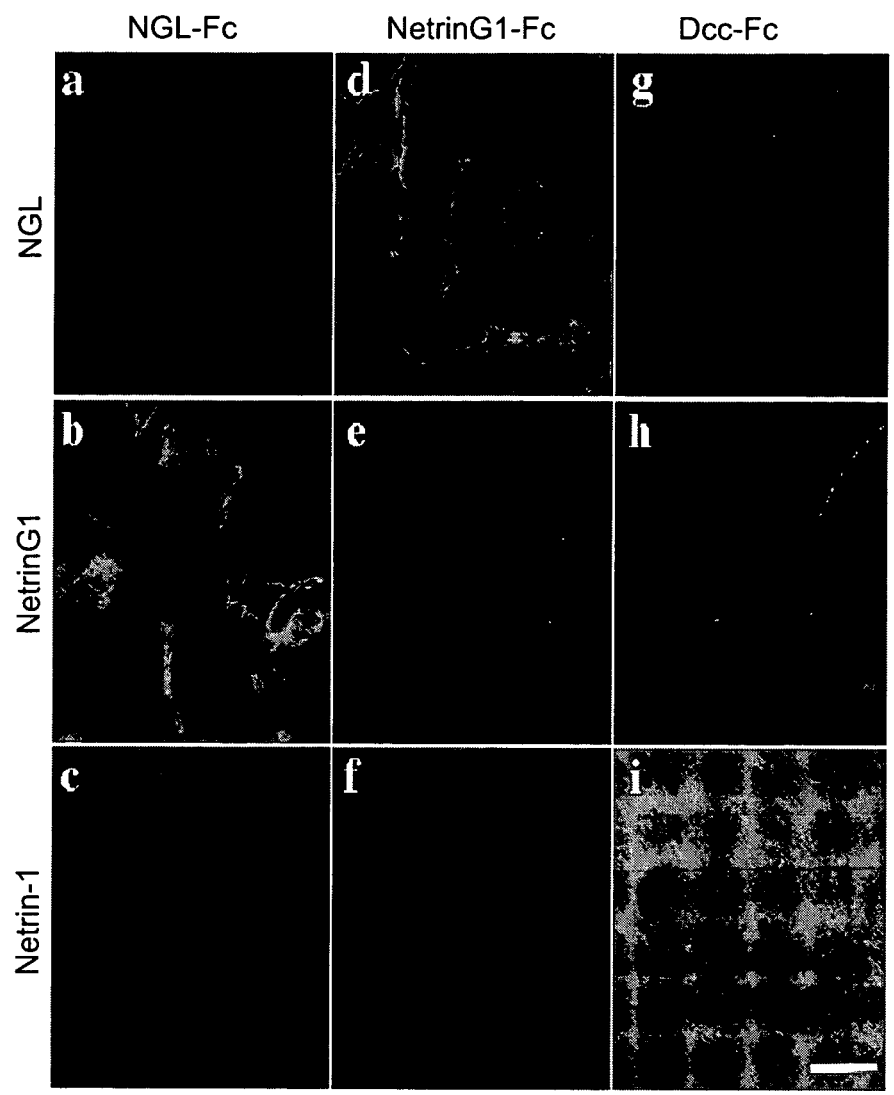
FIG. 1: Specific and direct interaction of NGL-1 and Netrin-G1 on cell surface
Figure 1:
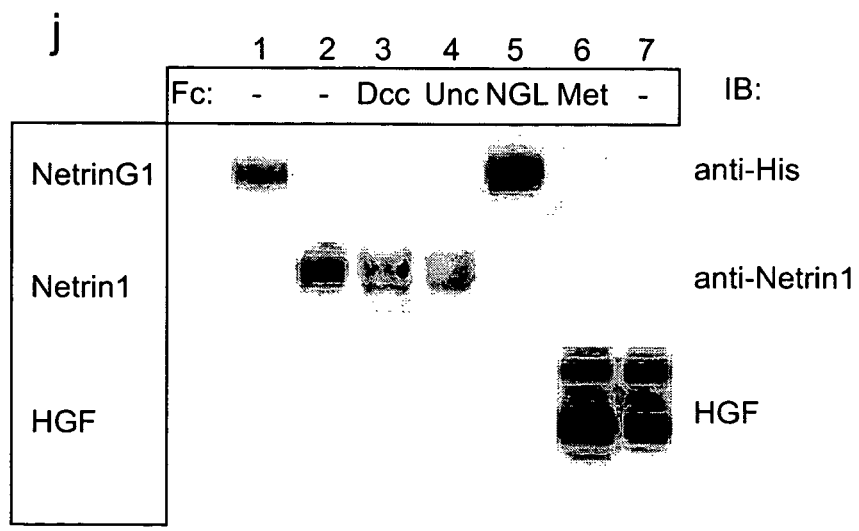

Recombinant human NGL-1-Fc (a-c), human Netrin-G1-Fc (d-f) and human DCC-Fc (g-i) were used to label COS7 cells expressing human NGL-1 (a, d, g), human Netrin-G1 (b, e, h), chicken Netrin-1 (c, f, i). Specific binding of the transfected cells was evident for Netrin-G1-expressing cells labeled with NGL-1-Fc (b), for NGL-1-expressing cells labeled with Netrin-G1-Fc (d), as well as for Netrin-1-expressing cells labeled with DCC-Fc (i). (j) The recombinant ECD-Fc fusion proteins (5 nM) indicated at the top (lanes 3-7) were incubated with human Netrin-G1-his (first row), chicken Netrin-1-his (second row) or human HGF protein (third row) in a solution binding assay. Complexes were pulled down by protein A-conjugated beads and probed with His-Probe (anti-His), antibodies to chicken netrin-1 and monoclonal antibodies to human HGF, as indicated. Direct and specific binding of NGL-1-Fc and netrin-G1-His (~50 kDa) is shown in the first row. The netrin-1-His protein (75-85 kDa) binds strongly to DCC-Fc and Unc5-Fc (lanes 3 and 4, second row), extremely weakly to NGL-1-Fc (lane 5, second row), and not at all to human cMet-Fc (lane 6). HGF binds to cMet-Fc (lane 6, third row). Lane 1, directly loaded netrin-G1-His; lane 2, directly loaded netrin-1-His; lane 7, directly loaded HGF.

FIG. 2: Characterization of interaction of NGL-1 and Netrin-G1

(a) Saturation curve and Scatchard analysis of human NGL-1-Fc protein solution (concentration in x-axis) to microtiter wells coated with human Netrin-G1-his protein. The y-axis (Bound) represents specific binding, i.e. total binding minus non-specific binding as determined by cMet-Fc binding to the wells in parallel. Inset, the Scatchard analysis of the data gave a Kd=1.6 nM. Linear regression yielded a correlation coefficient, r=0.96.

(b) A schematic diagram summarizes the predicted structure of the extracellular region of human NGL-1 protein. SS, signal sequence; LRR (leucine-rich repeat); NT, N-terminal domain of LRR; CT, C-terminal domain of LRR; Ig (immunoglobulin domain) and the ability of the different regions to bind Netrin G1.

Figure 3A:
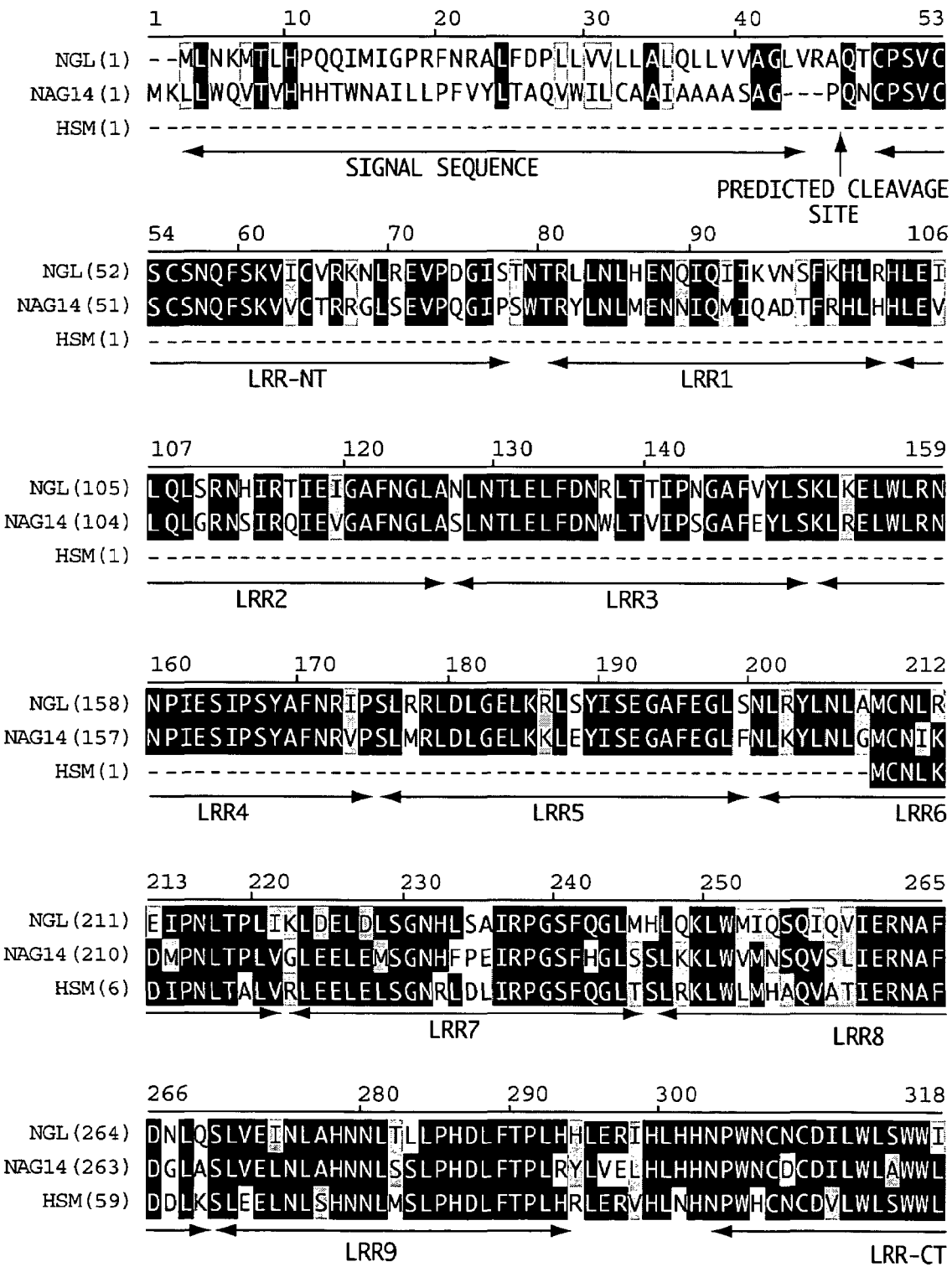

FIG. 3: Structure of NGL-1 and related molecules

The amino acid sequence alignment of the human NGL-1 (SEQ ID NO: 1) and related human proteins encoded by EST cDNAs. NAG14 (GenBank Accession Number AF196976; SEQ ID NO: 2) and another related EST, HSM (GenBank Accession Number HSM802162; SEQ ID NO: 3) are closely related to NGL-1. The identical amino acid residues are shaded in black and the conserved residues in gray. Underlined are the predicted structural domains and motifs. As shown, NGL-1 includes an N-terminal signal peptide at amino acid residues 1-42, nine leucine-rich repeats (LRRs) at amino acid residues, an Ig-like domain at amino acid residues 367-430, a transmembrane region at amino acid residues 563-589, an a C-terminal PDZ motif. Similar motifs for NSG14 and HSM are also shown.

FIG. 4: Sequence alignment of human, mouse and chicken NGL family members

Amino acid sequence alignment of human NGL-1 (SEQ ID NO: 1); mouse NGL (GanBank Accession Number AK032567; SEQ ID NO: 4); chicken NGL (SEQ ID NO: 5); human NAG14 (GenBank Accession Number AF196976; SEQ ID NO: 2) and mouse NAG14 (GenBank Accession Number AF300458; SEQ ID NO: 6). The chicken NGL protein sequence is derived from the partial cDNA clone by RT-PCR. The identical amino acid residues are shaded in black and the conserved residues in gray.

Figure 5:
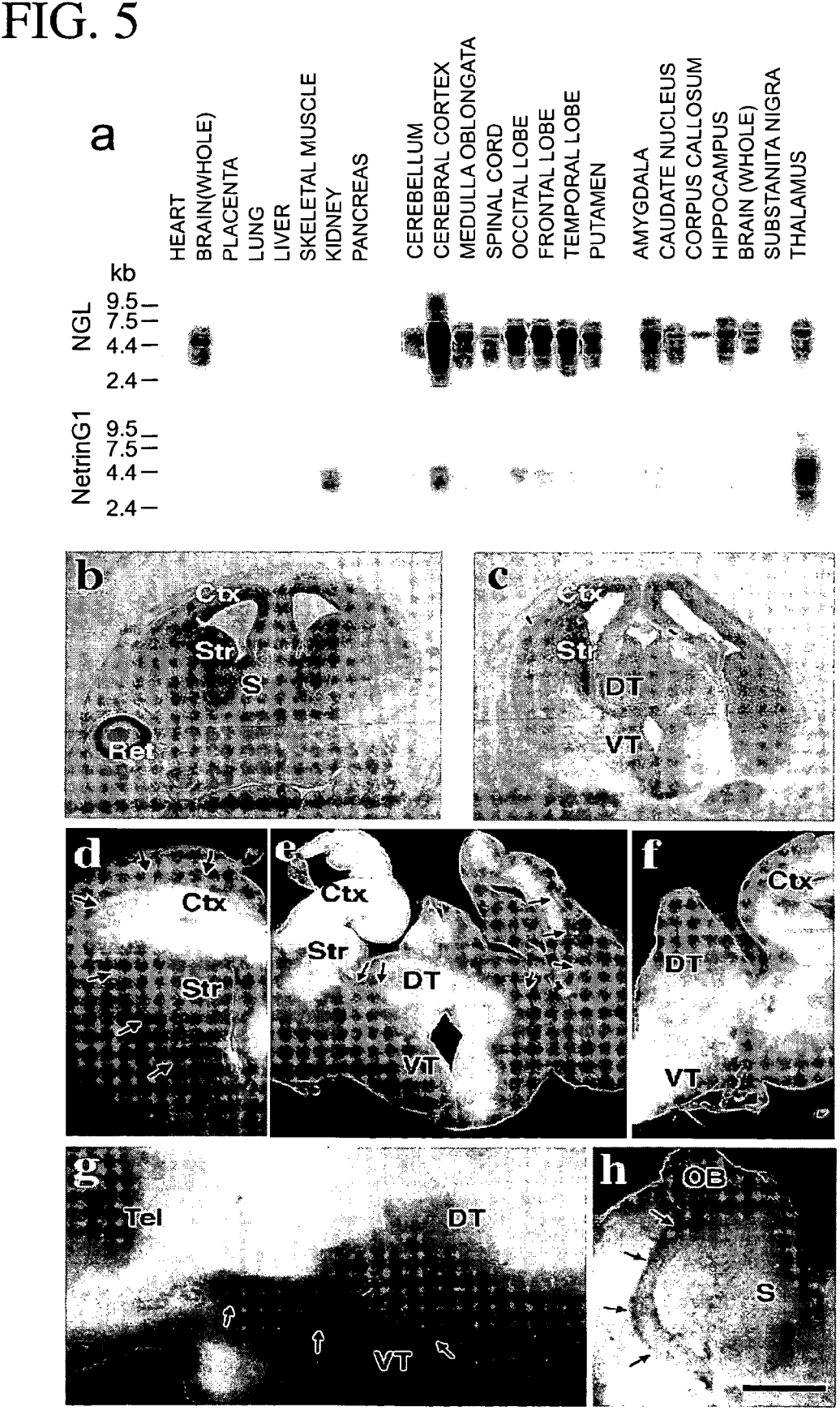

FIG. 5: Distribution of NGL-1, NetrinG1 transcripts and the endogenous NGL-1 binding activity (a) Northern analysis of NGL-1 and Netrin-G1 in adult human tissues and brain regions as indicated above each panel. (b, c) NGL-1 mRNA in situ hybridization of mouse brain at E14, hybridized with digoxigenin-labeled mouse NGL-1 riboprobe. Ctx, cerebral cortex; DT, dorsal thalamus; VT, ventral thalamus; Str, striatum; S, septal area; Ret, retina. (d-h) Endogenous NGL-1 binding activity as labeled by human NGL-1-Fc fusion protein using vibratome sections (d, e) or whole mount brain tissues (g, h). (g) is the lateral view of the E14 mouse brain, (h) is the ventral view of the E17 mouse brain. The brown color was developed by horseradish peroxidase (HRP)-conjugated anti-human IgG Fc and HRP substrate DAB. The arrows outline the thalamocortical axons in (d, e, g) and lateral olfactory tract in (h). Tel, telencephalon; OB, olfactory bulb. Other abbreviations are the same as in (b, c). (f) When human Netrin-G1-Fc fusion protein was used for labeling the vibratome sections at the similar axial level, the HRP signal was the same as the background level assessed by omitting Fc fusion protein in parallel experiments. Abbreviations are the same as in (b, c). Scale bar, 1 mm (b, c), 1.5 mm (d, e, f), 1.2 mm (g), 4 mm (h).

Figure 6:
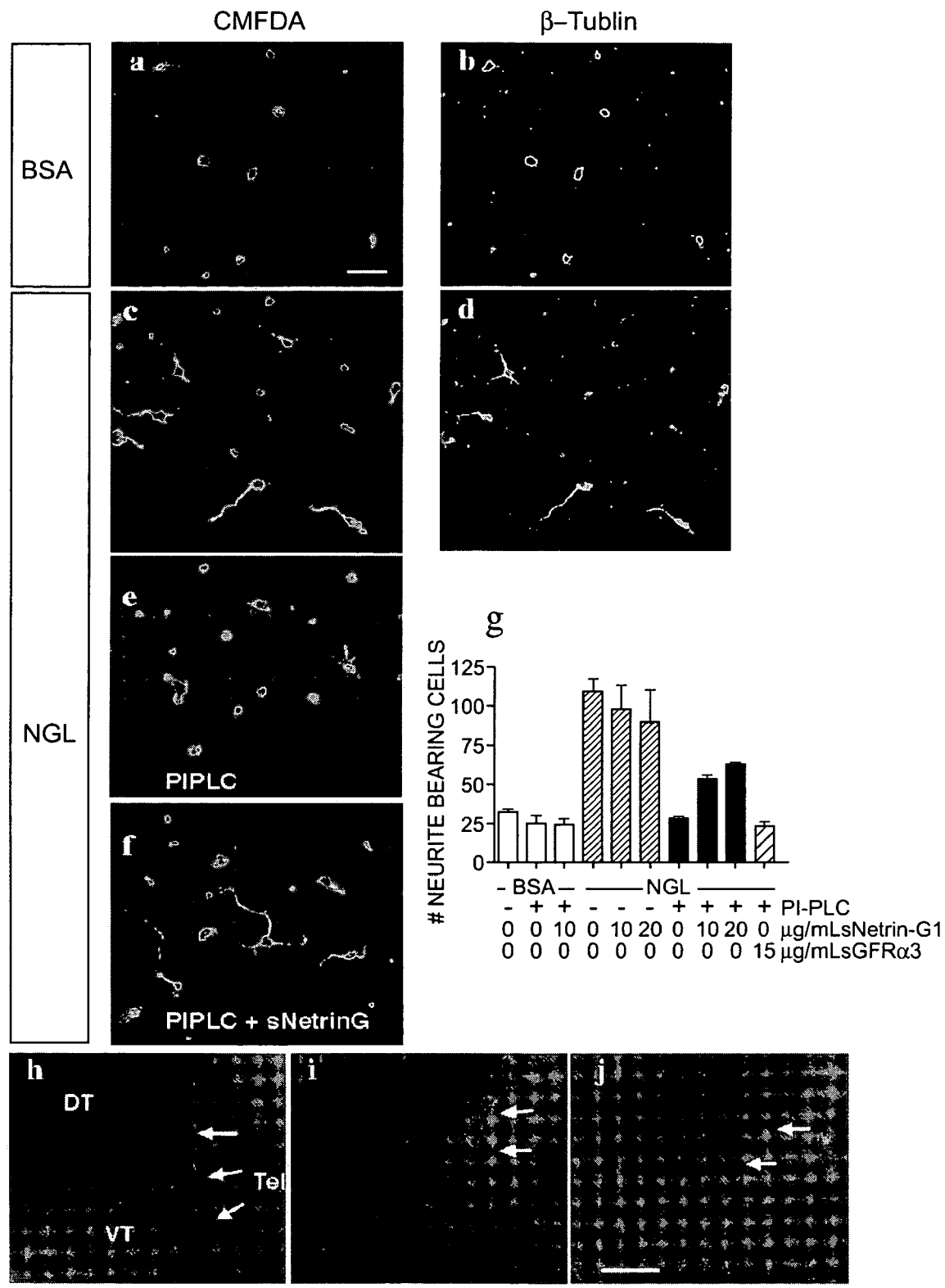

FIG. 6: Biological activity of NGL-1

(a-g) Dissociated cultures of E13-E14 mouse thalamic neurons grown on control bovine serum albumin (BSA) substrate (a, b) or on human NGL-1 substrate (c-f). Some of the cultures were treated with phosphotidylinositol-specific phospholipase C (PIPLC) (e, f) for 20 min before the addition of soluble Netrin-G1 (f) or soluble GFRα3 (g). 44-48 hours after the culture, the neurons were stained for the vital dye CM-FDA (a, c, e, f) or for the neuronal marker, anti-type III β-Tubulin (b, d). The great majority of live cells were positive for neuronal marker (90-95%) (g). (h-j) Chick thalamofugal axons (equivalent to the mammalian thalamocortical axons), whole mount stained by anti-Axonin-1 antibody, were significantly reduced when repeated injections of soluble human NGL-1-Fc protein were given (arrows in i, j). The control PBS-(h) or cMet-Fc (not shown) injected embryos showed normal pattern of thalamofugal axonal growth. DT, dorsal thalamus; VT, ventral thalamus; Tel, telencephalon. Scale bar, 50 μm (a-f), 0.2 mm (h-j).

DETAILED DESCRIPTION OF THE PREFERRED EMBODIMENTS

A. Definitions

Unless defined otherwise, technical and scientific terms used herein have the same meaning as commonly understood by one of ordinary skill in the art to which this invention belongs. See, e.g. Singleton et al., *Dictionary of Microbiology and Molecular Biology* 2nd ed., J. Wiley & Sons (New York, N.Y. 1994); Sambrook et al., *Molecular Cloning, A Laboratory Manual*, Cold Springs Harbor Press (Cold Springs Harbor, N.Y. 1989). For purposes of the present invention, the following terms are defined below.

The terms "PRO331," "NGL-1," and "NGL" are used interchangeably and encompass native sequence NGL-1 polypeptides and their functional derivatives.

A "native sequence NGL-1" or "native NGL-1" comprises a polypeptide having the same amino acid sequence as a NGL-1 derived from nature. Thus a native sequence NGL-1 can have the sequence of a human NGL-1 or NGL-1 from any other non-human animal, such as vertebrate, mammalian or avian species. The term specifically includes native human NGL-1 of SEQ ID NO: 1, mouse NGL-1 of SEQ ID NO: 4, chicken NGL-1 of SEQ ID NO: 5, all with or without the N-terminal methionine and with or without the N-terminal signal sequence. Such native sequence NGL-1 polypeptides can be isolated from nature or produced by recombinant and/or synthetic means. The term "native sequence NGL-1" specifically encompasses naturally occurring truncated forms (e.g. alternatively spliced forms), and naturally occurring allelic variants of the NGL-1. The preferred native sequence NGL-1 is the mature native sequence human NGL-1 of SEQ ID NO: 1.

A "functional derivative" of a native sequence polypeptide is a compound having a qualitative biological activity in common with the native sequence polypeptide. For the purpose of the present invention, a "functional derivative" of a native sequence NGL-1 polypeptide is defined by its ability to bind to and signal through a Netrin-G1 receptor. Thus, a "functional derivative" of NGL-1 is a functional ligand of Netrin-G1.

The functional derivatives include amino acid sequence variants (substitution, deletion and/or insertion variants) of a native sequence NGL-1, which preferably have at least about 60%, or at least about 70%, or at least about 80%, or at least about 85%, or at least about 90%, or at least about 95%, or at least about 98% or at least about 99% overall amino acid sequence identity with a native sequence NGL-1 polypeptide, such as a human NGL-1 (SEQ ID NO: 1); mouse NGL (SEQ ID NO: 4), or chicken NGL (SEQ ID NO: 5). Fragments of native sequence NGL-1 polypeptides are specifically included within the definition of functional derivatives, provided that they include at least the sequences of the corresponding native sequence NGL-1 that are required for binding to and signaling through a native Netrin-G1 receptor. Since soluble NGL-1 is capable of binding netrin-G1, but is not sufficient to activate the downstream signaling pathway, the functional derivatives preferably are membrane-bound proteins. Structure-function studies have shown that the Ig-like region within SEQ ID NO: 1 is not required for netrin-G1 binding, and that the last six C-terminal amino acids may be needed for activity. Accordingly, NGL-1 variants preferably retain these C-terminal amino acids but may lack all or part of the Ig-like region.

A specific group of NGL-1 functional derivatives includes NGL-1 amino acid sequence variants encoded by nucleic acid hybridizing under stringent conditions to the complement of nucleic acid encoding a native NGL-1 polypeptide.

Amino acid sequence variants of NGL-1 specifically include a polypeptide having at least 80%, or at least 85%, or at least 90%, or at least 95%, or at least 98%, or at least 99% sequence identity with amino acid residues 44-352 of SEQ ID NO: 1 and comprising a transmembrane region. Such amino acid sequence variants may further comprise a C-terminal PDZ domain-binding motif, such as a PDZ-binding motif having the sequence of VQETQI (SEQ ID NO: 7). Other amino acid variants comprise the extracellular domain (ECD) of a native sequence NGL-1, comprising nine leurine-rich repeats (LRRs). NGL-1 variants comprising amino acids 44-352, or 44-546 of SEQ ID NO: 1 are specifically included. Further amino acid sequence variants comprise amino acid residues 43-365, or 43-653 of human NAG14 (AF196976) of SEQ ID NO: 2. Yet another group of amino acid sequence variants include amino acid residues 1-147 of HSM (HSM802162) of SEQ ID NO: 3.

Functional derivatives further include fusion polypeptides including a native sequence or variant NGL-1 polypeptide (e.g. a fragment, such as the extracellular domain of a native sequence NGL-1) fused to a heterologous sequence, such as a tag or an immunoglobulin sequence as well as glycosylation variants of native sequence and variant NGL-1 polypeptides.

Glycosylation variants are NGL-1 polypeptides and polypeptide variants that differ in the extent of their glycosylation and/or in their glycosylation patterns. Glycosylation variants include polypeptides completely lacking in glycosylation (unglycosylated), variants having less glycosylated sites than the native form (deglycosylated) as well as variants in which the glycosylation has been changed. Included are deglycosylated and unglycosylated amino acid sequences variants, deglycosylated and unglycosylated native sequence NGL-1 molecules, and other glycosylation variants. For example, substitutional or deletional mutagenesis may be employed to eliminate the N- or O-linked glycosylation sites in the native sequence or variant NGL-1 molecule, e.g. the asparagine residue may be deleted or substituted for another basic residue such as lysine or histidine. Alternatively, flanking residues making up the glycosylation site may be substituted or deleted, even though the asparagine residues remain unchanged, in order to prevent glycosylation by eliminating the glycosylation recognition site. Additionally, unglycosylated NGL-1 polypeptides which have the glycosylation sites of a native molecule may be produced in recombinant prokaryotic cell culture because prokaryotes are incapable of introducing glycosylation into polypeptides.

Glycosylation variants may be produced by selecting appropriate host cells or by in vitro methods. Yeast and insect cells, for example, introduce glycosylation which varies significantly from that of mammalian systems. Similarly, mammalian cells having a different species or tissue origin than the source of the NGL-1 polypeptide are routinely screened for the ability to introduce variant glycosylation as characterized for example by elevated levels of mannose or variant ratios of mannose, fucose, sialic acid, and other sugars typically found in mammalian glycoproteins.

The term "Netrin-G1" encompasses native sequence Netrin-G1 and its functional derivatives. Functional derivatives are defined as discussed above for NGL-1, and include "Native sequence Netrin-G1" or "native Netrin-G1" comprises a polypeptide having the same amino acid sequence as a Netrin-G1 derived from nature. Thus a native sequence Netrin-G1 can have the sequence of a human Netrin-G1 or Netrin-G1 from any other non-human animal, such as vertebrate, mammalian or avian species. Native sequence Netrin-G1 is well known in the art, see, for example, Nakashiba, T. et al., "Netrin-G1: a novel glycosyl phosphatidylinositol-linked mammalian netrin that is functionally divergent from classical netrins", *J. Neurosci* 20 6540-6550 (2000) and Yin et al., "Laminets: laminin- and netrin-related genes expressed in distinct neuronal subsets", *Mol. Cell. Neurosci* 1 9 344-358 (2002) which are expressly incorporated by reference herein. Such native sequence Netrin-G1 polypeptides can be isolated from nature or produced by recombinant and/or synthetic means. The term "native sequence Netrin-G1" specifically encompasses naturally occurring truncated forms of the Netrin-G1, naturally occurring allelic variants of the Netrin-G1. The preferred native sequence Netrin-G1 is a mature native sequence of human Netrin-G1 of SEQ ID NO: 8.

Just as in the case of NGL-1, functional derivatives include amino acid sequence variants, fusion polypeptides, and glycosylation variants.

Preferred amino acid sequence variants of Netrin-G1 have at least about 60%, or at least about 70%, or at least about 80%, or at least about 85%, or at least about 90%, or at least about 95%, or at least about 98% or at least about 99% overall amino acid sequence identity with a native sequence Netrin-G1 polypeptide, such as the human Netrin-G1 polypeptide of SEQ ID NO: 8, as long as they retain a qualitative biological activity in common with a native sequence Netrin-G1 polypeptide. A preferred biological activity is the ability to bind to and mediate the biological activity of a native sequence NGL-1.

The term "immunoadhesin" and refers to a chimeric molecule that combines a portion of a ligand or receptor, e.g. NGL-1 or Netrin-G1 (generally the extracellular domain thereof) with an immunoglobulin sequence. The immunoglobulin sequence preferably, but not necessarily, is an immunoglobulin constant domain sequence. The immunoglobulin moiety in the chimeras of the present invention may be obtained from IgG1, IgG2, IgG3 or IgG4 subtypes, IgA, IgE, IgD or IgM, but preferably IgG1 or IgG3. Thus, for example, the Ig portion of an IgG1 immunoadhesin may comprise the CH1, hinge, CH2 and CH3 sequences, or hinge, CH2 and CH3 sequences of the immunoglobulin constant region.

The term "epitope-tagged" when used herein refers to a chimeric polypeptide comprising a polypeptide, such as NGL-1 or Netrin-G1, fused to a "tag polypeptide". The tag polypeptide has enough residues to provide an epitope against which an antibody thereagainst can be made, yet is short enough such that it does not interfere with biological activity of the NGL-1 or Netrin-G1. The tag polypeptide preferably also is fairly unique so that the antibody raised against it does not substantially cross-react with other epitopes. Suitable tag polypeptides generally have at least six amino acid residues and usually between about 8-50 amino acid residues (preferably between about 9-30 residues). Preferred are poly-histidine sequences, which bind nickel or other transient metals, allowing isolation of the tagged protein by Ni-NTA or other transient metal chromatography as described (Lindsay et al. Neuron 17:571-574 (1996)), for example.

"Isolated NGL-1." or "isolated Netrin-G1" means material that has been purified from a natural source or has been prepared by recombinant or synthetic methods and is sufficiently free of other peptides or proteins (1) to obtain at least 15 and preferably 20 amino acid residues of the N-terminal or of an internal amino acid sequence by using a spinning cup sequential or the best commercially available amino acid sequential marketed or as modified by published methods as of the filing date of this application, or (2) to homogeneity by SDS-PAGE under non-reducing or reducing conditions using Coomassie blue or, preferably, silver stain. Homogeneity here means less than about 5% contamination with other source proteins "Essentially pure" protein means a composition comprising at least about 90% by weight of the protein, based on total weight of the composition, preferably at least about 95% by weight. "Essentially homogeneous" protein means a composition comprising at least about 99% by weight of protein, based on total weight of the composition.

"Percent amino acid sequence identity" is defined herein as the percentage of amino acid residues in the candidate sequences that are identical with the residues in the Netrin-G1 or NGL-1 sequence, after aligning the sequences and introducing gaps, if necessary, to achieve the maximum percent sequence identity, and not considering any conservative substitutions as part of the sequence identity. Percent amino acid sequence identity is calculated for the full-length of the Netrin-G1 or NGL-1 sequence. Thus, shorter sequences, even if they show 100% sequence identity with a portion of the Netrin-G1 of NGL-1 sequence will be less than 100% identical with those sequences.

The term "agonist" is used herein in the broadest sense. An "NGL-1 agonist" is a molecule which partially or fully mimics a biological activity of a native sequence NGL-1 polypeptide. NGL-1 agonists include, without limitation, agonist antibodies specifically binding NGL-1, peptides, small inorganic molecules, and the like.

The term "antagonist" is used herein in the broadest sense. An NGL-1 "antagonist" is a molecule, which partially or fully bocks, inhibits, neutralizes, prevents or interferes with a biological activity of NGL-1, regardless of the underlying mechanism. For the purpose of the present invention, the biological activity preferably is the ability to Antagonists of NGL-1 can be identified, for example, based upon their ability to inhibit, block, or reverse binding of NGL-1 to Netrin-G1. For example a culture of activated TCA (thalamocortical axons) cells can be incubated with Netrin G1, in the presence and absence of a test compound, and NGL-1 binding monitored in the cell culture. If the NGL-1 binding even is lower in the presence of the test compound than in its absence, the test compound is an NGL-1 antagonist. Furthermore, NGL-1 antagonists can be identified in functional assays, by measuring NGL-1 biological activity. Examples of NGL-1 antagonists include, without limitation, neutralizing antibodies against the native sequence NGL-1 polypeptide, immunoadhesins comprising a soluble NGL-1 fused to an immunoglobulin constant region sequence, small molecules, antisense oligonucleotides capable of inhibiting translation and/or transcription of a gene encoding a NGL-1 polypeptide, oligonucleotide decoys, etc.

"Antisense oligodeoxynucleotides" or "antisense oligonucleotides" (which terms are used interchangeably) are defined as nucleic acid molecules that can inhibit the transcription and/or translation of target genes in a sequence-specific manner. The term "antisense" refers to the fact that the nucleic acid is complementary to the coding ("sense") genetic sequence of the target gene. Antisense oligonucleotides hybridize in an antiparallel orientation to nascent mRNA through Watson-Crick base-pairing. By binding the target mRNA template, antisense oligonucleotides block the successful translation of the encoded protein. The term specifically includes antisense agents called "ribozymes" that have been designed to induce catalytic cleavage of a target RNA by addition of a sequence that has natural self-splicing activity (Warzocha and Wotowiec, "Antisense strategy: biological utility and prospects in the treatment of hematological malignancies." *Leuk. Lymphoma* 24:267-281 [1997]).

"Oligonucleotide decoy" molecules, also referred to a transcription factor oligonucleotide decoys (TF ODNs) are small double-stranded oligonucleotides that are introduced into cells to specifically bind to target transcription factors, thereby, preventing these factors from transactivating their target genes.

"Native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one and ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., J. Mol. Biol., 186:651-663 (1985); Novotny and Haber, Proc. Natl. Acad. Sci. USA, 82:4592-4596 (1985)).

The term "variable" refers to the fact that certain portions of the variable domains differ extensively in sequence among antibodies and are used in the binding and specificity of each particular antibody for its particular antigen. However, the variability is not evenly distributed through the variable domains of antibodies. It is concentrated in three segments called complementarity determining regions (CDRs) or hypervariable regions both in the light chain and the heavy chain variable domains. The more highly conserved portions of variable domains are called the framework (FR). The variable domains of native heavy and light chains each comprise four FR regions, largely adopting a b-sheet configuration, connected by three CDRs, which form loops connecting, and in some cases forming part of, the b-sheet structure. The CDRs in each chain are held together in close proximity by the FR regions and, with the CDRs from the other chain, contribute to the formation of the antigen binding site of antibodies (see Kabat et al., Sequences of Proteins of Immunological Interest, National Institute of Health, Bethesda, Md. (1987)). The constant domains are not involved directly in binding an antibody to an antigen, but exhibit various effector functions, such as participation of the antibody in antibody-dependent cellular toxicity.

Papain digestion of antibodies products two identical antigen binding fragments, called "Fab" fragments, each with a single antigen binding site, and a residual "Fc" fragment, whose name reflects its ability to crystallize readily. Pepsin treatment yields an F(ab').sub.2 fragment that has two antigen combining sites and is still capable of cross-linking antigen.

"Fv" is the minimum antibody fragment which contains a complete antigen recognition and binding site. This region consists of a dimer of one heavy and one light chain variable domain in tight, non-covalent association. It is in this configuration that the three CDRs of each variable domain interact to define an antigen binding site on the surface of the $V_H$-VL dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab" fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other, chemical couplings of antibody fragments are also known.

The "light chains" of antibodies (immunoglobulins) from any vertebrate species can be assigned to one of two clearly distinct types, called kappa and lambda (1), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called alpha, delta, epsilon, gamma and .mu., respectively. The subunit structures and three-dimensional configurations of different classes of immunoglobulins are well known.

The term "antibody" is used in the broadest sense and specifically covers single monoclonal antibodies (including agonist and antagonist antibodies), antibody compositions with polyepitopic specificity, as well as antibody fragments (e.g., Fab, F(ab')$_2$, scFv and Fv), so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler & Milstein, Nature, 256:495 (1975), or may be made by recombinant DNA methods (see, e.g., U.S. Pat. No. 4,816,567 (Cabilly et al.)).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity, e.g. binding to and activating mp1 (U.S. Pat. No. 4,816,567 (Cabilly et al.); and Morrison et al., Proc. Natl. Acad. Sci. USA, 81:6851-6855 (1984)).

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Furthermore, humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details see: Jones et al., Nature, 321:522-525 (1986); Reichmann et al., Nature, 332: 323-329 (1988); and Presta, Curr. Op. Struct. Biol., 2:593-596 (1992)).

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun in The Pharmacology of Monoclonal Antibodies, vol. 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$ and $V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA 90:6444-6448 (1993).

The expression "linear antibodies" when used throughout this application refers to the antibodies described in Zapata et al. Protein Eng. 8(10): 1057-1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

The terms "treat" or "treatment" refer to both therapeutic treatment and prophylactic or preventative measures, wherein the object is to prevent or slow down (lessen) an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

"Chronic" administration refers to administration of the agent(s) in a continuous mode as opposed to an acute mode, so as to maintain the desired effect for an extended period of time.

"Intermittent" administration is treatment that is not consecutively done without interruption, but rather is cyclic in nature.

Administration "in combination with" one or more further therapeutic agents includes simultaneous (concurrent) and consecutive administration in any order.

A "subject" is a vertebrate, preferably a mammal, more preferably a human.

The term "mammal" is used herein to refer to any animal classified as a mammal, including, without limitation, humans, non-human primates, domestic and farm animals, and zoo, sports, or pet animals, such as sheep, horses, cows, pigs, cats, dogs, etc. Preferably, the mammal herein is human.

An "effective amount" is an amount sufficient to effect beneficial or desired therapeutic (including preventative) results. An effective amount can be administered in one or more administrations.

B. Modes of Carrying Out the Invention

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", $2^{nd}$ edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", $4^{th}$ edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991).

The present invention, at least in part, is based on the identification of the interaction between the transmembrane ligand NGL-1 and Netrin-G1 as essential for the growth of thalamocortical axons.

Figure 2A:
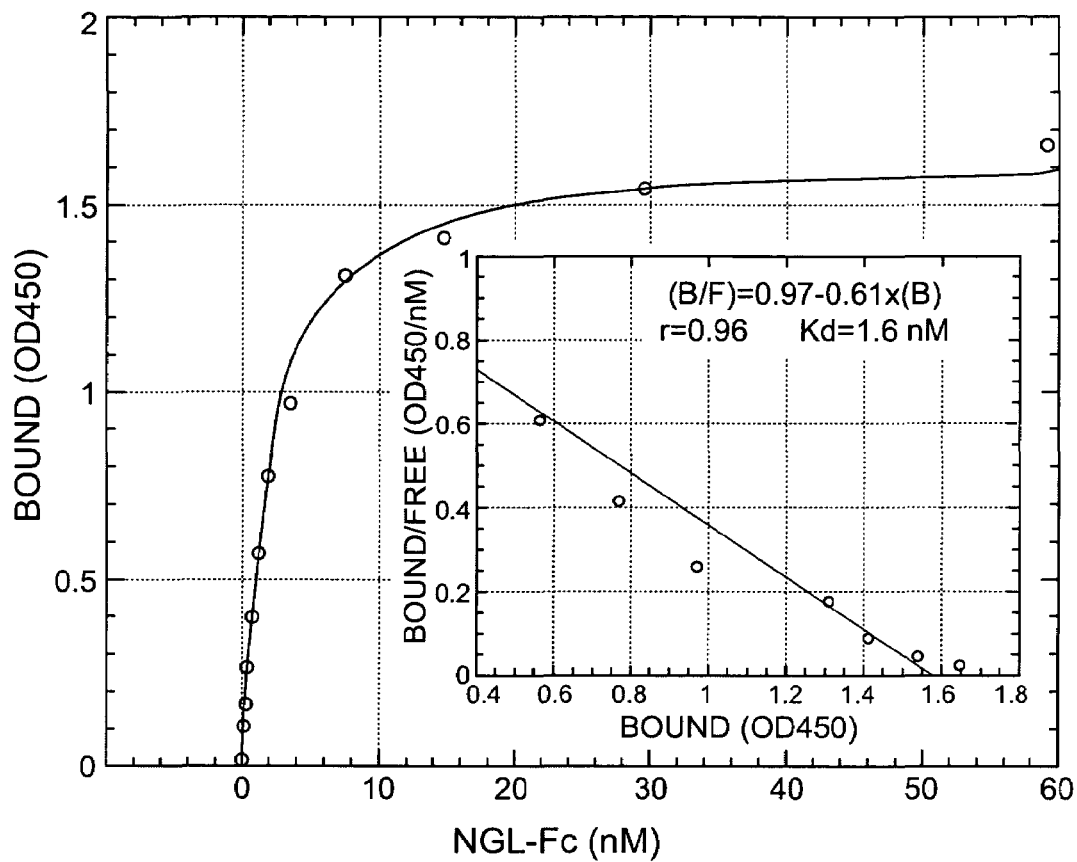
Figure 2B:
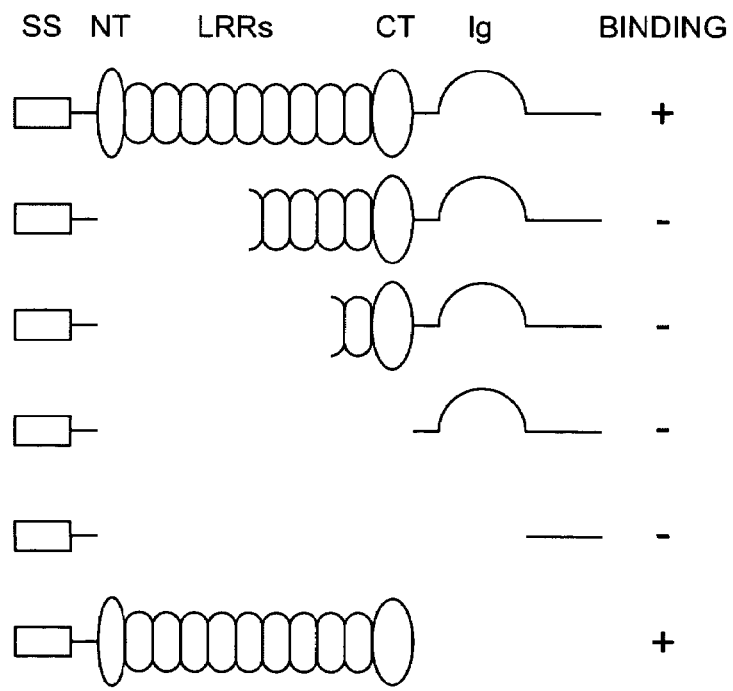

NGL-1 Native human NGL-1 was originally disclosed as "PRO331" encoded by DNA40981-1234 in U.S. provisional application Ser. Nos. 60/065,186 filed on Nov. 12, 1997, 60/066,770 filed on Nov. 24, 1997 and 60/088,026 filed on Jun. 4, 1998, and in PCT application publication No. WO 99/14328, published on Mar. 25, 1999. DNA40981 was deposited with the American Type Culture Collection (ATCC), Manassas, Va., USA, on Nov. 7, 1997, and assigned ATCC Deposit No. 209439. NGL-1 has been shown to inhibit VEGF-stimulated proliferation of endothelial cell growth (WO 99/14328, published Mar. 25, 1999 and WO 00/14796, published Mar. 23, 2000), exhibited prolinflammatory activity in a skin vascular permeability assay (WO 01/04311, published Jan. 18, 2001), and stimulated immune response in the mixed lymphocyte reaction (MLR) assay (WO 01/19991, published Mar. 22, 2001). The human NGL-1 cDNA encodes a type I transmembrane protein with an N-terminal signal sequence, a single transmembrane domain of 640 amino acid residues and a predicted molecular weight of 71.9 kDa (FIG. 2b and FIG. 3, SEQ ID NO: 1). The ECD of NGL-1 consists of 9 leucine rich repeats (LRR) with the flanking LRR N-terminal domain (LRR-NT) and LRR C-terminal domain (LRR-CT), followed by an immunoglobulin domain (Ig domain). The 92 amino acid cytoplasmic region does not contain any obvious structural consensus sequence except that the C-terminus sequence "ETQI" (SEQ ID NO: 8) is a potential PDZ-domain binding motif.

Native human Netrin-G1 was originally disclosed as "PRO1133" encoded by DNA53913-1490 in U.S. provisional application Ser. No. 60/097,952 filed on Aug. 26, 1998. DNA53913-1490 was deposited with ATCC, Manassas, Va., USA, on Aug. 25, 1998, and assigned ATCC Deposit No. 203162. See also, Nakashiba et al., *J. Neurosci.* 20:6540-6550 (2000) and Yin et al., *Dev. Biol.* 208:430-440 (1999). Several splice variants of Netrin-G1 have been detected, and it was reported that none of the multiple isoforms of netrin-G1 binds DCC or Unc5, the known netrin receptors (Nakashiba et al., supra).

Netrin-G1 and NGL-1 were identified as a receptor-ligand pair in Example 171 of PCT application Publication No. 00/73454, published on Dec. 7, 2000. The same information is present in PCT application Publication No. 01/68848, published on Sep. 20, 2001. In particular, a novel high-throughput protein interaction assay was utilized to identify native sequence human NGL-1, a novel LRR- and Ig domain-containing transmembrane protein, as a specific binding partner of native sequence human Netrin-G1, as described in the examples below.

The present invention demonstrates, for the first time, the role of the Netrin-G1/NGL-1 receptor/ligand pair in promoting the outgrowth of thalamic axons.

Variants of native sequence NGL-1 and Netrin-G1 can be prepared by methods known in the art. Thus, amino acid sequence variants are polypeptides having an amino acid sequence which differs from a native sequence by virtue of the insertion, deletion, and/or substitution of one or more amino acid residues within a native sequence. Amino acid sequence variants may be prepared synthetically, such as by introducing appropriate nucleotide changes into a previously isolated NGL-1 or Netrin-G1 DNA, or by in vitro synthesis of the desired variant polypeptide. As indicated above, such variants will comprise deletions from, or insertions or substitutions of, one or more amino acid residues within the amino acid sequence of a native NGL-1 or Netrin-G1 polypeptide. Any combination of deletion, insertion, and substitution is made to arrive at a desired amino acid sequence variant, provided that the resulting variant polypeptide possesses a desired characteristic. The amino acid changes also may result in further modifications of NGL-1 or Netrin-G1 upon expression in recombinant hosts, e.g. introducing or moving sites of glycosylation, or introducing membrane anchor sequences (in accordance with PCT WO 89/01041 published Feb. 9, 1989).

There are two principal variables to consider in making such predetermined mutations: the location of the mutation site and the nature of the mutation. In general, the location and nature of the mutation chosen will depend upon the characteristic to be modified. For example, candidate NGL-1 antagonists or super agonists initially will be selected by locating amino acid residues that are identical or highly conserved among NGL-1 and related native polypeptides, such as, for example, NAG14 or HSM. Those residues then will be modified in series, e.g., by (1) substituting first with conservative choices and then with more radical selections depending upon the results achieved, (2) deleting the target, residue, or (3) inserting residues of the same or different class adjacent to the located site, or combinations of options 1-3.

One helpful technique is called "ala scanning". Here, an amino acid residue or group of target residues are identified and substituted by alanine or polyalanine. Those domains demonstrating functional sensitivity to the alanine substitutions then are refined by introducing further or other variants at or for the sites of alanine substitution. While the site for introducing an amino acid sequence variation is predetermined, the nature of the mutation per se need not be predetermined. For example, to optimize the performance of a mutation at a given site, ala scanning or random mutagenesis is conducted at the target codon or region and the expressed NGL-1 variants are screened for the optimal combination of desired activity.

Amino acid sequence deletions generally range from about 1 to 30 residues, more preferably about 1 to 10 residues, and typically are contiguous. Deletions may be introduced into regions of low homology among NGL-1 and related native polypeptides, such as NAG14 or HSM to modify the activity of NGL-1. Deletions from NGL-1 in areas of substantial homology with structurally related polypeptides will be more likely to modify the biological activity of NGL-1 more significantly. The number of consecutive deletions will be selected so as to preserve the tertiary structure of NGL-1 in the affected domain, e.g., beta-pleated sheet or alpha helix.

Amino acid sequence insertions include amino- and/or carboxyl-terminal fusions ranging in length from one residue to polypeptides containing a thousand or more residues, as well as intrasequence insertions of single or multiple amino acid residues. Intrasequence insertions (i.e., insertions within the mature NGL-1 sequence) may range generally from about 1 to 10 residues, more preferably 1 to 5, most preferably 1 to 3. An example of a terminal insertion includes fusion of a heterologous N-terminal signal sequence to the N-terminus of the NGL-1 molecule to facilitate the secretion of mature NGL-1 from recombinant hosts. Such signals generally will be homologous to the intended host cell and include STII or Ipp for E. coli, alpha factor for yeast, and viral signals such as herpes gD for mammalian cells. Other insertions include the fusion of an immunogenic polypeptide such as a bacterial or yeast protein to the N- or C-termini of NGL-1.

The third group of variants are those in which at least one amino acid residue in NGL-1, and preferably only one, has been removed and a different residue inserted in its place. An example is the replacement of arginine and lysine by other amino acids to render the NGL-1 resistant to proteolysis by serine proteases, thereby creating a variant of NGL-1 that is more stable. The sites of greatest interest for substitutional mutagenesis include sites where the amino acids found in NGL-1 and structurally related polypeptides are substantially different in terms of side chain bulk, charge of hydrophobicity, but where there also is a high degree of homology at the selected site within various animal analogues of native human NGL-1.

Amino acid sequence variants of native sequence Netrin-G1 can be designed and made in a similar manner.

1. Screening Assays to Identify NGL-1 Agonists

This invention includes the use of NGL-1 and its agonists, and screening assays to identify NGL-1 agonists.

Screening assays for agonist drug candidates may be designed to identify compounds that bind or complex with Netrin-G1 (including a subunit or other fragment thereof) and mimic a qualitative biological activity of native NGL-1, or otherwise enhance the interaction of Netrin-G1 with NGL-1, thereby enhancing NGL-1 biological activity, such as the production and/or functioning of neurons. The screening assays provided herein include assays amenable to high-throughput screening of chemical libraries, making them particularly suitable for identifying small molecule drug candidates. Generally, binding assays and activity assays are provided.

The assays can be performed in a variety of formats, including, without limitation, protein-protein binding assays (including competitive binding assays), biochemical screening assays, immunoassays, and cell-based assays, which are well characterized in the art.

All assays for agonists are common in that they call for contacting the drug candidate with a native sequence Netrin-G1 polypeptide, or a fragment of such polypeptide, under conditions and for a time sufficient to allow these two components to interact, and measuring an NGL-1 biological activity.

In binding assays, the interaction is binding, and the complex formed can be isolated or detected in the reaction mixture. In a particular embodiment, either the Netrin G1 or NGL-1 polypeptide or the drug candidate is immobilized on a solid phase, e.g., on a microtiter plate, by covalent or non-covalent attachments. Non-covalent attachment generally is accomplished by coating the solid surface with a solution of the Netrin-G1 or NGL-1 polypeptide and drying. Alternatively, an immobilized antibody, e.g., a monoclonal antibody, specific for the Netrin-G1 polypeptide or the NGL-1 polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound is a polypeptide which interacts with but does not bind to Netrin-G1 or the NGL-1 receptor, its interaction with the respective polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature (London)*, 340:245-246 (1989); Chien et al., *Proc. Natl. Acad. Sci. USA*, 88:9578-9582 (1991)) as disclosed by Chevray and Nathans, *Proc. Natl. Acad. Sci. USA*, 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

The NGL-1 agonists can be identified, for example, based upon their ability to enhance axon growth, especially the outgrowth of thalamic, such as thalamocortical axons.

A special group of NGL-1 agonists includes amino acid sequences variants of native sequence NGL-1 molecules.

Another special group of NGL-1 agonists includes agonist antibodies, such as, for example, agonist anti-NGL-1 antibodies. By "agonist antibody" is meant an antibody which is able to bind to a native sequence NGL-1 polypeptide, and signal through a Netrin-G1 receptor in vitro and/or in vivo. Preferred agonist antibodies herein have the ability to promote the outgrowth of thalamocortical axons.

2. Anti-NGL-1 Antibodies

As discussed above, in a particular embodiment, the NGL-1 agonists are monoclonal antibodies to NGL-1 (e.g. a subunit of NGL-1), including antibody fragments. Antibodies to the ECD of NGL-1 are specifically within the scope of the invention.

Methods for making monoclonal antibodies are well known in the art. Thus, monoclonal antibodies may be prepared using hybridoma methods, such as those described by Kohler and Milstein, *Nature,* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the NGL-1 polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice,* Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, *J. Immunol.,* 133:3001 (1984); Brodeur et al., *Monoclonal Antibody Production Techniques and Applications,* Marcel Dekker, Inc., New York, (1987) pp. 51-63].

The culture medium in which the hybridoma cells are cultured can then be assayed for the presence of monoclonal antibodies directed against NGL-1 receptor. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.,* 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking. In vitro methods are also suitable for preparing monovalent antibodies.

The anti-NGL-1 antibodies of the invention may further be humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature,* 321:522-525 (1986); Riechmann et al., *Nature,* 332:323-329 (1988); and Presta, *Curr. Op. Struct. Biol.,* 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522-525 (1986); Riechmann et al., *Nature*, 332:323-327 (1988); Verhoeyen et al., *Science*, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86-95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779-783 (1992); Lonberg et al., *Nature* 368 856-859 (1994); Morrison, *Nature* 368, 812-13 (1994); Fishwild et al., *Nature Biotechnology* 14, 845-51 (1996); Neuberger, *Nature Biotechnology* 14, 826 (1996); Lonberg and Huszar, *Intern. Rev. Immunol.* 13 65-93 (1995).

Mendez et al. (*Nature Genetics* 15: 146-156 (1997)) have further improved the technology and have generated a line of transgenic mice designated as "Xenomouse II" that, when challenged with an antigen, generates high affinity fully human antibodies. This was achieved by germ-line integration of megabase human heavy chain and light chain loci into mice with deletion into endogenous $J_H$ segment as described above. The Xenomouse II harbors 1,020 kb of human heavy chain locus containing approximately 66 $V_H$ genes, complete $D_H$ and $J_H$ regions and three different constant regions (μ, δ and χ), and also harbors 800 kb of human κ locus containing 32 Vκ genes, Jκ segments and Cκ genes. The antibodies produced in these mice closely resemble that seen in humans in all respects, including gene rearrangement, assembly, and repertoire. The human antibodies are preferentially expressed over endogenous antibodies due to deletion in endogenous $J_H$ segment that prevents gene rearrangement in the murine locus.

Alternatively, the phage display technology (McCafferty et al., *Nature* 348, 552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g. Johnson, Kevin S. and Chiswell, David J., *Current Opinion in Structural Biology* 3, 564-571 (1993). Several sources of V-gene segments can be used for phage display. Clackson et al., *Nature* 352, 624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222, 581-597 (1991), or Griffith et al., *EMBO J.* 12, 725-734 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., *Bio/Technol.* 10, 779-783 [1992]). In this method, the affinity of "primary" human antibodies obtained by phage display can be improved by sequentially replacing the heavy and light chain V region genes with repertoires of naturally occurring variants (repertoires) of V domain genes obtained from unimmunized donors. This techniques allows the production of antibodies and antibody fragments with affinities in the nM range. A strategy for making very large phage antibody repertoires has been described by Waterhouse et al., *Nucl. Acids Res.* 21, 2265-2266 (1993).

Various techniques have been developed for the production of antibody fragments. Traditionally, these fragments were derived via proteolytic digestion of intact antibodies (see, e.g., Morimoto et al., *J. Biochem. Biophys. Methods* 24:107-117 (1992) and Brennan et al., *Science* 229:81 (1985)). However, these fragments can now be produced directly by recombinant host cells. For example, Fab'-SH fragments can be directly recovered from *E. coli* and chemically coupled to form F(ab')$_2$ fragments (Carter et al., *Bio/Technology* 10:163-167 (1992)). In another embodiment, the F(ab')$_2$ is formed using the leucine zipper GCN4 to promote assembly of the F(ab')$_2$ molecule. According to another approach, Fv, Fab or F(ab')$_2$ fragments can be isolated directly from recombinant host cell culture. Other techniques for the production of antibody fragments will be apparent to the skilled practitioner.

Heteroconjugate antibodies, composed of two covalently joined antibodies, are also within the scope of the present invention. Such antibodies have, for example, been proposed to target immune system cells to unwanted cells (U.S. Pat. No. 4,676,980), and for treatment of HIV infection (PCT application publication Nos. WO 91/00360 and WO 92/200373). Heteroconjugate antibodies may be made using any convenient cross-linking methods, using well known, commercially available cross-linking agents.

For further information concerning the production of monoclonal antibodies see also Goding, J. W., *Monoclonal Antibodies: Principles and Practice*, 3rd Edition, Academic Press, Inc., London, San Diego, 1996; Liddell and Weeks: *Antibody Technology: A Comprehensive Overview*, Bios Scientific Publishers: Oxford, UK, 1995; Breitling and Dubel: *Recombinant Antibodies*, John Wiley & Sons, New York, 1999; and *Phage Display: A Laboratory Manual*, Barbas et al., editors, Cold Springs Harbor Laboratory, Cold Spring Harbor, 2001.

The agonist antibodies of the invention may be selected, for example, by immobilizing a Netrin-G1 receptor and then panning a library of human scFv prepared as described above using the immobilized receptor to bind antibody. Griffiths et. al., EMBO-J, 1993, 12:725-734. The specificity and activity of specific clones can be assessed using known assays. After a first panning step, one obtains a library of phage containing a plurality of different single chain antibodies displayed on phage having improved binding to the receptor. Subsequent panning steps provide additional libraries with higher binding affinities. When avidity effects are a problem, monovalent phage display libraries may be used in which less than 20%, preferably less than 10%, and more preferably less than 1% of the phage display more than one copy of an antibody on the surface of the phage. Monovalent display can be accomplished with the use of phagemid and helper phage as described, for example, in Lowman et. al., Methods: A Companion to Methods in Enzymology, 1991, 3(3):205-216. A preferred phage is M13 and display is preferably as a fusion protein with coat protein 3 as described in Lowman et. al., supra. Other suitable phage include fl and fd filamentous phage. Fusion protein display with other virus coat proteins is also known and may be used in this invention. See U.S. Pat. No. 5,223,409.

3. Target Diseases

Thalamocortical axons originate in dorsal thalamus, and project ventrally in diencephalon and then dorsolaterally in ventral telencephalon to their target, the neocortex.

Netrin G1 and NGL-1 have been implicated in various neural diseases, including, without limitation, Alzheimer's disease, Parkinsons's disease, Huntington's chorea, amyotrophic lateral sclerosis (ALS), peripheral neuropathies, and other conditions characterized by neurodegeneration or loss of neurons. In addition, the composition may be useful in treating damaged nerve cells, e.g., nerves damaged by medical conditions such as strokes, diabetes mellitus, liver or kidney dysfunction or other endocrine/metabolic derangements, and the toxic effect of chemotherapy or radiation used to treat cancer, HIV and AIDS.

Target diseases for treatment with NGL-1 or agonists thereof include, without limitation, benign or malignant brain tumors of any cellular origin and of any location, optionally combined with surgical, chemical and/or radiological treatment of such tumors; mechanical trauma of the nervous system (including the brain, spinal cord, nerve roots, peripheral ganglia and peripheral nerves) that impinges upon, or disrupts the integrity of any axonal pathways, including the thalamo-cortical pathway; chemical intoxication of the nervous system affecting axons, such as mercury and lead; congenital or hereditary abnormalities of the nervous system affecting axonal growth or function, such as, for example, Charcot-Marie-Tooth diseases; autoimmune diseases attacking the axons of the central or peripheral nervous system, such as multiple sclerosis and Gullian-Barre syndrome; viral, bacterial or parasitic infections of the nervous system with damage to the axons, such as acute or chronic meningitis, encephalitis or neuritis caused by herpes simplex virus, HIV, tuberculosis and/or leprosy.

4. Pharmaceutical Compositions

NGL-1, antibodies specifically binding an NGL-1 receptor, as well as other NGL-1 agonist molecules identified by the screening assays disclosed hereinbefore, can be administered for the treatment of various disorders, in particular the target diseases listed above, in the form of pharmaceutical compositions.

Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA,* 90: 7889-7893 (1993).

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's *Pharmaceutical Sciences*, supra.

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The formulation herein may also contain more than one active compound as necessary for the particular indication being treated, preferably those with complementary activities that do not adversely affect each other. Such molecules are suitably present in combination in amounts that are effective for the purpose intended, or may be formulated separately, and administered concurrently or consecutively, in any order.

For example, the NGL-1 agonists of the present invention may be administered in combination with anti-neural agents and other active compounds currently in use for the treatment of the target diseases and conditions discussed above.

The following example is offered for illustrative purposes only, and is not intended to limit the scope of the present invention in any way.

All patent and literature references cited in the present specification are hereby incorporated by reference in their entirety.

EXAMPLES

All cDNA plasmids and proteins used in the following examples were generated using standard molecular biological methods, or obtained from commercial vendors.

The soluble GFRα3 protein was kindly provided by D. Stone (Rinat Neuroscience). Recombinant cMet-Fc fusion protein and recombinant 6× His-tagged chick Netrin-1 protein were from R&D Systems.

Example 1

Specific and Direct Interaction between Netrin-G and NGL-1

The extracellular domain (ECD) of a group of ~300 secreted or transmembrane human proteins was fused with the constant region of human immunoglobulin G (IgG Fc). The ECD of selected cDNAs were fused in frame with the human IgG1 Fc region in the pRK5 vector for mammalian expression or in pHIF (Pharmingen) for baculoviral production. The recombinant human ECD-Fc and -his fusion proteins were produced by the baculoviral expression system as described [Lee, J. et al. IL-17E, a novel proinflammatory ligand for the IL-17 receptor homolog IL-17Rh1. *J Biol Chem* 276, 1660-4. (2001)], or produced in HEK293 cells and purified by Ni-NTA column (Qiagen).

The resultant fusion proteins were expressed and used in binding assays over a panel of ~400 putative cell surface transmembrane or GPI-anchored cell surface human proteins that were transiently expressed in COS7 cells. Purified ECD-Fc fusion proteins (0.5 µg/ml) or the crude baculovirus lysates were added to transiently transfected COS7 cells for 1-2 hours at room temperature. After 3 rinses with cold phosphate buffered saline (PBS), the bound protein was cross-linked to the cell surface with 4% paraformaldehyde. The bound Fc fusion protein was detected by biotinylated anti-human IgGFc and R-phycoerythrin-conjugated streptavidin (Jackson Immunoresearch). Cell surface staining was visualized by fluorescent microscopy and images were taken with the Penguin 800CL digital camera system (Pixera).

One cDNA clone corresponding to the "c" splice isoform of human Netrin-G1, which is structurally related to the Netrin family of axon guidance molecules [Nakashiba, T. et al. Netrin-G1: a novel glycosyl phosphatidylinositol-linked mammalian netrin that is functionally divergent from classical netrins. *J. Neurosci.* 20, 6540-6550. (2000)], when expressed in COS cells, was specifically labeled by the ECD of a novel transmembrane protein, named NGL-1. In fact, the human NGL-1 was the only protein that bound the human Netrin-G1 expressing COS cells in this screen.

Although the NGL-1 and Netrin-G1 interaction appeared to be specific within the context of the screen, the classical Netrins and their known receptors, DCC and Unc5, were not included in the screen. Thus whether NGL-1 also interacts with Netrin-1 and its receptors was determined. Using the same cell surface binding assay, NGL-1, Netrin-G1, or Netrin-1 were expressed in COS7 cells (rows in FIGS. 1*a-i*) and their ability to bind the IgG Fc fusion protein of NGL-1, Netrin-G1, or DCC (columns in FIGS. 1*a-i*) was determined. The NGL-1-ECD IgG Fc fusion protein only bound COS cells expressing Netrin-G1, but not cells that expressed NGL-1, Netrin-1 or DCC (FIG. 1*a-c* and data not shown). Likewise, the Netrin-G1-Fc fusion protein bound only COS cells that expressed NGL-1, but not cells that expressed Netrin-G1, DCC or netrin (FIG. 1*d-f* and data not shown). Finally, DCC-Fc only bound to COS cells expressing Netrin-1, but not to cells expressing NGL-1, Netrin-G1 or DCC (FIGS. 1*g-I*, and data not shown). These results indicate that the interaction between Netrin-G1 and NGL-1is specific even within the Netrin superfamily and that Netrin-G1 and NGL-1 do not display homophilic interactions.

It was noted that the labeling of Netrin-1-expressing-cell by DCC-Fc was diffuse (FIG. 1*i*) due to Netrin-1 secretion and its affinity to heparin-like molecules on neighboring cell surface [Serafini, T. et al. The netrins define a family of axon outgrowth-promoting proteins homologous to *C. elegans* UNC-6. *Cell* 78, 409-424. (1994)]. In contrast, the labeling of NGL-1 or Netrin-G1 -expressing cells was fairly discrete (FIG. 1*b, d*) despite the fact that they also exhibited affinities to dextran and heparin-like molecules (by BIAcore, data not shown), suggesting that NGL-1 and Netrin-G1 are not released quantitatively from the surface of their respective producing cells.

The question remained whether Netrin-G1 and NGL-1 directly interact with each other. Purified Netrin-G1 protein with a C-terminus His tag ("NetrinG-his") was generated and was incubated with purified NGL-1-Fc. Recombinant ECD-Fc fusion proteins (5 nM) indicated at the top (FIG. 1*j*, lanes 3-7) were incubated with 5 nM of human Netrin-G1-his (first row), chicken Netrin-1-his (second row) or human HGF protein (third row) in a solution binding assay. The protein mixtures, each at 1-2 nM final concentration, were incubated at room temperature for 30 min, and then 1 uL of the protein A beads (Pierce) was added to each mixture. The bound protein A beads were then washed 3 times with the wash buffer by centrifugation and resuspension. The wash buffer consists of 50 mM NaCl, 10 mM TrisCl (pH7.5), 1 mM EDTA and 0.1% Triton X-100. Equal volume of the protein complexes were loaded and the blot was probed with HisProbe ("anti-His") (Qiagen), anti-chicken Netrin-1 (R&D Systems) or an anti-human HGF monoclonal antibody (anti-HGF) (Genentech) as indicated to the right in FIG. 1.

The NetrinG-his protein could be precipitated by NGL-1-Fc fusion protein (FIG. 1*j*, first row) but not by DCC-Fc, Unc5h-Fc, or Met-Fc. As expected, DCC-Fc and Unc5h-Fc, but not NGL-1-Fc, could precipitate Netrin-1 (Netrin1-his, FIG. 1*j*, second row). Also as expected, Met-Fc precipitated its ligand the hepatocyte growth factor (HGF) (FIG. 1*j*, third row).

Direct and specific binding of NGL-1-Fc and Netrin-G1-his (~50 kDa) is shown in the first row. The Netrin1-his protein (75-85 kDa) binds strongly to DCC-Fc and Unc5-Fc (lanes 3-4, second row), extremely weakly with NGL-1-Fc (lane 5, second row), and not at all to human cMet-Fc (lane 6). HGF binds cMet-Fc (lane 6, third row). Therefore, NGL-1 and Netrin-G1 interact directly without any requirement for additional factors.

Example 2

Cell Expression

To directly confirm that NGL-1 is membrane bound, NGL-1 was epitope-tagged at the N-terminus immediately following the signal sequence and expressed in HEK293 cells. Although a full length NGL-1 protein was detected in the total cell lysate, little or no epitope-tagged NGL-1 was detected in the medium. In contrast, secreted myc-tagged Netrin-1 was readily detectable in the cell culture medium).

Therefore, most if not all of the NGL-1 protein is retained on the surface of the NGL-1 expressing cells.

Example 3

The Binding Affinity of NGL-1

The binding affinity of NGL-1 and Netrin-G1 was then evaluated by a solid phase binding assay. Crude NetrinG-his protein (1 μg/ml) was coated in microtiter wells and non-specific binding sites saturated with 0.5% BSA. Purified NGL-1-Fc protein was serially diluted and added to the coated wells for 1 hour. Signals were detected with the biotinylated anti-human IgGFc antibody, horseradish peroxidase-conjugated strepavidin and a chromogenic substrate TMB (Kirkgaard and Perry Lab). The reactions were terminated with phosphoric acid and absorbance at 450 nm was measured. Non-specific binding was determined in parallel by omitting the microtiter well coating or by incubating the wells with the irrelevant cMet-Fc fusion protein, and dissociation constants were determined using saturation curves and Scatchard analysis (FIG. 2a). NGL-1 and Netrin-G1 were found to interact with an apparent $K_d$ of 1.6 nM, a value that is of the same order of magnitude as the interaction between Netrin1-Fc and DCC (5.2 nM) [Keino-Masu, K. et al. Deleted in Colorectal Cancer (DCC) encodes a netrin receptor. *Cell* 87, 175-185. (1996)].

Example 4

The Structure of NGL-1

Full length human NGL-1 and Netrin-G1 cDNA clones were initially isolated through screening cDNA libraries by virtue of the presence of putative signal sequences.

FIG. 2b shows a schematic diagram summarizing the predicted structure of the extracellular region of human NGL-1 protein. SS, signal sequence; LRR (leucine-rich repeat); NT, N-terminal domain of LRR; CT, C-terminal domain of LRR; Ig (immunoglobulin domain).

The human NGL-1 cDNA encodes a putative type I transmembrane protein with an N-terminal signal sequence, a single transmembrane domain of 640 amino acid residues and a predicted molecular weight of 71.9 kDa (FIG. 2b and FIG. 3). The ECD of NGL-1 consists of 9 leucine rich repeats (LRR, residues 77-291) with the flanking LRR N-terminal domain (LRR-NT, residues 46-75) and LRR C-terminal domain (LRR-CT, residues 301-352), followed by an immunoglobulin domain (Ig domain 367-428). This is followed by a TM (transmembrane region), and PDZ motif (potential PDZ domain-binding motif). The 92 amino acid cytoplasmic region does not contain any obvious structural consensus sequence except that the C-terminus sequence "ETQI" is a potential PDZ-domain binding motif.

To determine which portion of the NGL-1 molecule mediates Netrin-G1 binding, we generated various deletion constructs in the ECD of NGL-1 and tested their ability to bind Netrin-G1 in both cell surface and solution binding assays (FIG. 2b). The results from both assays were identical and indicated that the LRR region, but not the Ig domain, of NGL-1 is both necessary and sufficient for the interaction with Netrin-G1. The protein expression of all deletion constructs was verified by western blot.

Example 5

Sequence Analysis

BLAST search identified additional human cDNAs that showed similarity to the human NGL-1 sequence (FIG. 3). In particular, human NAG14 (GenBank Accession No. AF196976, SEQ ID NO: 2) is a cDNA down regulated in brain tumors, and it is 51% identical, 89% similar to human NGL-1. A third cDNA, HSM (GenBank Accession No. HSM802162, SEQ ID NO: 3), appears to be a partial clone but the available sequence also showed 54% identity to NGL-1 and 50% identity to human NAG14. These cDNAs together define a distinct human LRR-containing transmembrane protein family.

The human NGL-1 clone was found to be identical to a cDNA clone in the GenBank. (Accession Number AB046800, SEQ ID NO: 1).

A mouse EST clone (GenBank accession no. AW210185, IMAGE Consortium, SEQ ID NO: 4) similar to human NGL-1 was identified by BLAST. The entire mouse EST clone was sequenced and found to be over 99.9% identical to the human NGL-1 in the amino acid sequence, representing the mouse ortholog of human NGL-1.

The partial mouse NAG14 homologue and the partial chick NGL-1 cDNA were cloned by degenerate RT-PCR using E15 mouse whole brain and E5-6 chick telencephalon as the source of RNA respectively. Full length human DCC, Netrin-1 and unc5h3 clones were amplified from cDNA libraries.

By degenerate RT-PCR, we also cloned a partial cDNA of the chick NGL-1 gene. The amino acid sequence alignment of the human NGL-1 and related human proteins encoded by EST cDNAs shown in FIGS. 3 and 4 shows that human and mouse NAG14 (SEQ ID NOS: 2 and 6) and another related EST, HSM (GenBank Accession Number HSM802162, SEQ ID NO: 3) are closely related to NGL-1. The identical amino acid residues are shaded in black and the conserved residues in gray. Underlined are the predicted structural domains and motifs. Therefore the NGL-1 gene is conserved among the vertebrate species.

The closest invertebrate gene similar to NGL-1 is the *Drosophila* kek3, a hypothetical gene predicted by the *Drosophila* Genome Project, but these two proteins do not show any similarity outside the LRR region. In this regard it is noteworthy that there is no Netrin-G1 homologue identified in either the *Drosophila* or *C. elegans* genome [Nakashiba, T. et al. Netrin-G1: a novel glycosyl phosphatidylinositol-linked mammalian netrin that is functionally divergent from classical netrins. *J. Neurosci.* 20, 6540-6550. (2000)]. Therefore, NGL-1 and Netrin-G1 are probably recent addition to the genome during animal evolution.

Example 6

Distribution of NGL-1 mRNA and NGL-1-Binding Activity in vivo

Next the distribution of NGL-1 and Netrin-G1 transcripts in a panel of fetal and adult human RNA samples was examined (FIG. 5a).

Adult and fetal human RNA panels were from Clontech, and the filters were hybridized with $^{32}$P-labeled human NGL-1 and Netrin-G1 probes according to the manufacturer's instructions. NGL-1 mRNA was detected specifically in the fetal and adult brain tissue as two bands of 3.5 and 4.8 kb.

On the other hand, Netrin-G1 was highly expressed in the developing and adult thalamus (FIG. 5a and previously published data [Nakashiba, T. et al. Netrin-G1: a novel glycosyl phosphatidylinositol-linked mammalian netrin that is functionally divergent from classical netrins. *J. Neurosci.* 20, 6540-6550. (2000)]). This complementary pattern of expression raised the possibility that NGL-1-NetrinG1 interaction may be involved in the development and/or the mature functions of the thalamocortical axons.

To investigate the developmental expression of NGL-1, we turned to the mouse embryos (FIG. 5b, c). Mouse NGL-1 cDNA was used to prepare digoxinin-labeled riboprobe for in situ hybridization with frozen sections of E14 CD1 mouse brain. Timed pregnant CD 1 mice were from Hilltop and Charles River.

Crude NGL-1-Fc and Netrin-G1-Fc protein preps were added to freshly dissected whole mount E12-E18 mouse brain in the presence of 0.01% Tween-20 to enhance Fc protein penetration. Alternatively, freshly dissected brains were imbedded in 3% agarose in HBSS to prepare 200 μm Vibratome sections, which were then incubated with the Fc-fusion proteins. After several gentle washes in PBS, the tissues were fixed with 4% paraformaldehyde and the endogenous HRP activity was quenched by 0.03% $H_2O_2$. Bound Fc fusion protein was detected by HRP-conjugated anti-human IgGFc and DAB substrate (Sigma).

The mouse NGL-1 mRNA was highly expressed in the developing cerebral cortex (Ctx) and the striatum (Str) at E14 and the individual neocortical areas such as the frontal, parietal and occipital lobes. Putamen, amydala, hippocampus and medulla oblongata exhibited a moderate level of NGL-1 mRNA expression. Caudate nucleus and thalamus expressed NGL-1 at a low level, whereas other brain regions exhibited very weak or no expression of NGL-1. As expected, Netrin-G1 mRNA was highly expressed in the thalamus with very low or no expression in most of the other tissue or brain regions examined. The developing striatum has been proposed to be an intermediate target and the cerebral cortex is the final target for TCAs [Metin, C. & Godement, P. The ganglionic eminence may be an intermediate target for corticofulgal and thalamocortical axons. *J. Neurosci* 16, 3219-3235. (1996)].

In further support of this hypothesis, we found that the E14 mouse TCAs specifically bound NGL-1 (FIG. 5d-g). The NGL-1-Fc-bound structures followed the classical trajectory of TCAs from the dorsal thalamus (DT) through the ventral thalamus, the striatum into the cerebral cortex, although the mass of dorsal thalamus per se was not labeled under the same experimental conditions (FIG. 5e). This result showed that the endogenous NGL-1-binding activity is highly concentrated in the axons, not the cell bodies, of the thalamic projection neurons. In addition, NGL-1-Fc also labeled the lateral olfactory tracts (LOT) coursing over the ventral surface of the E17 mouse forebrain in the stereotypical arc pattern (FIG. 5h). Since Netrin-G1 mRNA is highly expressed in the dorsal thalamus, which projects the TCAs, and in the mitral cells of the olfactory bulb, which give rise to the axons in the LOT, the axonal Netrin-G1 protein is likely to be the predominant NGL-1 binding activity.

Since the human NGL-1 and NAG14 genes share high sequence similarity as well as the same overall domain structures, we cloned a cDNA of the mouse homologue of NAG14 and used a region that is divergent between NGL-1 and NAG14 as the probe for in situ hybridization. This mouse NAG14 probe showed an identical pattern of expression to that of NGL-1 in the E14 forebrain.

Example 7

NGL-1 Promote Neurite Outgrowth of the Thalamic Neurons via Netrin-G1

To test whether NGL-1 and Netrin-G1 are involved in the development of thalamic axons, we used the dissociated thalamic neuronal culture system Dorsal thalamic neurons from embryonic day 13.5 (E13.5) mice were dissociated and grown on 96 well tissue culture plates pre-coated with designated substrates for ~2 days. They were then labeled with the vital dye 5-chloromethylflourorecein diacetate (CM-FDA, Molecular Probes) and the neuronal marker anti-type III β-Tubulin (Chemicon). Viable neurons bearing at least one neurite 2 times the cell body diameter were counted using the TE300 inverted microscope (Nikon). Statistical analysis was performed using Instat software (GraphPad).

FIG. 6a-g shows dissociated cultures of E13-14 mouse thalamic neurons grown on control bovine serum albumin (BSA) substrate (a, b) or on human NGL-1 substrate (c-f). Some of the cultures were treated with PIPLC (e, f) for 20 min before the addition of soluble Netrin-G1 (f) or soluble GFRα3 (g). 44-48 hours after the culture, the neurons were stained for the vital dye CM-FDA (a, c, e, f) or for the neuronal marker, anti-type III β-Tubulin (b, d). The great majority of live cells were positive for neuronal marker (90-95%). (g) The number of live neurons bearing neuites in each culture condition was counted using the criterion that includes only the cells positive for CM-FDA staining and with the longest neurite at least twice the length of the widest cell body diameter.

When E13 mouse thalamic neurons were grown on a control substrate of Bovine Serum Albumin (BSA), few neurons extended neurites over a period of 42-48 hours in culture (FIG. 6a-b). By contrast, many process-bearing thalamic neurons were observed when NGL-1 protein was immobilized as the substrate for neuronal culture (FIG. 6c-d). Similar numbers of live cells were observed with the live dye CM-FDA in the presence or absence of NGL-1 substrate (223±22 and 238±17 cells per well for BSA and NGL-1 substrate respectively). This neurite outgrowth activity, however, appeared to be dependent on GPI-anchored protein(s) present on the surface of the thalamic neurons as phosphatidylinositol phospholipase C (PIPLC) treatment dramatically reduced the number of the process-bearing neurons (FIG. 6e). To test if the GPI-anchored Netrin-G1 is an essential co-receptor mediating the NGL-1-induced neurite outgrowth, we drew analogy to the GDNF receptor system in which a high concentration of soluble GFRα component can partially restore the signaling activity after PIPLC treatment[15]. Indeed a high concentration of soluble Netrin-G1 protein (sNetrinG, added at 10-20 μg/mL), but not soluble GFRα3 (at 15 μg/mL), was capable of partially restoring the NGL-1-stimulated neurite outgrowth in PIPLC treated thalamic neurons (FIG. 6f-g, P<0.01, F=13.87, One-way ANOVA test). Netrin-G1 has no effect on thalamic neurons grown on BSA or neurons grown on NGL-1 without PIPLC treatment (FIG. 6g). These results strongly suggested that the surface bound NGL-1 can promote neurite outgrowth of developing thalamic neurons and that such activity is at least partially dependent upon the GPI-anchored Netrin-G1 present on the thalamic neurons.

Example 8

Soluble NGL-1 Blocks the Growth of Thalamic Axons in vivo

Finally the question was asked whether the interaction of NGL-1 and Netrin-G1 is required for the growth of TCAs in vivo. To this aim the chick embryos were used as an experimental system. The avian dorsal thalamus also gives rise to a prominent bundle of thalamofugal axons that project to the telencephalon and can be visualized with the anti-Axonin-1 antibody.

Fertilized Leghorn chicken eggs were from Charles River/SPAFAS. Starting from Hamburger-Hamilton stage 12 (embryonic day 1.5), 0.2-1 µg of NGL-1-Fc or cMet-Fc fusion protein was injected daily into the prosencephlic vesicle of the chick neural tube. At stages 25-26 (day 5.5), the brains were dissected and analyzed by whole mount immunohistochemistry with anti-Axonin-1 antibody (Developmental Study Hybridoma Bank).

We injected the soluble NGL-1-Fc or Netrin-G1-Fc protein into the neural tube of the chick embryos daily starting from HH stages 10-12 and analyzed the thalamofugal axons at stages 25-26 with anti-Axonin antibody (FIG. 6h-i). A substantial number of the NGL-1-Fc injected embryos exhibited severe reduction in Axonin-1-positive thalamofugal axons (n=21/67, or 31%) (FIG. 6i-j) as compared with the embryos injected with PBS or a control Met-Fc (n=2/42, or 5%) (FIG. 6h). This difference is statistically significant (P=0.0007, Fisher's exact test). On the other hand, Netrin-G1-Fc injected embryos still maintained a normal pattern of thalamofugal axons (not shown), consistent with the observation that excess of soluble Netrin-G1 protein did not affect NGL-1-induced neurite outgrowth of the murine thalamic neurons (FIG. 6g).

These experiments further support the importance of the NGL-1/NetrinG1 interaction in the development of thalamic axons.

While the present invention has been described with reference to what are considered to be the specific embodiments, it is to be understood that the invention is not limited to such embodiments. To the contrary, the invention is intended to cover various modifications and equivalents included within the spirit and scope of the appended claims.

What is claimed is:

1. A method of promoting axonal growth or regeneration comprising delivering to an injured neuron an effective amount of a Netrin G1 Ligand polypeptide (NGL-1 polypeptide) that comprises a non-human homologue of NGL-1 selected from the group consisting of SEQ ID NO: 4, SEQ ID NO: 4 lacking the N-terminal methionine, SEQ ID NO: 4 lacking an N-terminal signal sequence consisting of the amino acid sequence of residues 1-42 of SEQ ID NO:4, SEQ ID NO: 4 lacking all or part of the immunoglobulin-like region consisting of the amino acid sequence of residues 364-428 of SEQ ID NO:4, glycosylation variants thereof, and a fusion peptide comprising any of said preceding polypeptides fused to a heterologous amino acid sequence, where the NGL-1 polypeptide comprises a transmembrane region, and wherein said NGL-1 polypeptide is effective to bind to and signal through a Netrin-G1 receptor.

2. The method of claim 1 wherein said polypeptide comprises an extracellular domain (ECD) comprising nine leucine-rich repeats (LRRs) consisting of the amino acid sequence of residues 81-295 of SEQ ID NO:4.

3. The method of claim 1 wherein the N-terminal signal sequence consists of the amino acid sequence of residues 1-42 of SEQ ID NO:4.

4. A method of promoting axonal growth or regeneration comprising delivering to an injured neuron an effective amount of a Netrin G1 Ligand polypeptide (NGL-1 polypeptide) that comprises a non-human homologue of NGL-1, wherein the NGL-1 polypeptide comprises a transmembrane region, and wherein said NGL-1 polypeptide is effective to bind to and signal through a Netrin-G1 receptor, wherein said non-human homologue is mouse NGL-1 (SEQ ID NO: 4).

5. The method of claim 1 wherein said neuron is a thalamic neuron.

* * * * *